(12) United States Patent
Beauvais et al.

(10) Patent No.: US 9,839,738 B2
(45) Date of Patent: Dec. 12, 2017

(54) TRANSFORMER IRRIGATION/ASPIRATION DEVICE

(71) Applicant: Novartis AG, Basel (CH)

(72) Inventors: Charles Kittridge Beauvais, West Lawn, PA (US); G. Lamar Kirchhevel, Laguna Hills, CA (US)

(73) Assignee: Novartis AG, Basel (CH)

( * ) Notice: Subject to any disclaimer, the term of this patent is extended or adjusted under 35 U.S.C. 154(b) by 92 days.

(21) Appl. No.: 14/272,784

(22) Filed: May 8, 2014

(65) Prior Publication Data

US 2014/0364799 A1 Dec. 11, 2014

Related U.S. Application Data

(60) Provisional application No. 61/831,665, filed on Jun. 6, 2013.

(51) Int. Cl.
*A61M 3/02* (2006.01)
*A61M 1/00* (2006.01)
(Continued)

(52) U.S. Cl.
CPC ....... *A61M 3/0283* (2013.01); *A61F 9/00736* (2013.01); *A61M 1/0039* (2013.01);
(Continued)

(58) Field of Classification Search
CPC .............. A61M 1/0039; A61M 1/0064; A61M 1/0084; A61M 1/0086; A61M 1/0088; A61M 3/0283; A61F 9/00736
See application file for complete search history.

(56) References Cited

U.S. PATENT DOCUMENTS 3,109,426 A 11/1963 Noonan et al.
3,264,907 A 8/1966 Mueller et al.
(Continued)

FOREIGN PATENT DOCUMENTS

CN 101083961 A 12/2007
CN 101677854 A 3/2010
(Continued)

OTHER PUBLICATIONS

International Searching Authority, International Search Report, PCT/US2014/037293, Sep. 26, 2014, 2 pages.
(Continued)

*Primary Examiner* — Nathan R Price
*Assistant Examiner* — Justin L Zamory

(57) ABSTRACT

In various embodiments, a cannula device includes an irrigation handpiece portion (with a first aspiration tip for aspiration and an irrigation fluid outlet for irrigation) and an aspiration handpiece portion (configured to aspirate fluid into a second aspiration tip that extends from a distal end of the aspiration handpiece portion). The cannula device is transformable between: (a) a coaxial mode in which the aspiration handpiece portion is coupled to the irrigation handpiece portion such that fluid is aspirated through the first aspiration tip and then the second aspiration tip in series and irrigation fluid is provided through the irrigation fluid outlet, and (b) a bimanual mode in which the aspiration handpiece portion is separated from the irrigation handpiece portion to provide aspiration through the second aspiration tip while the irrigation handpiece portion continues to provide irrigation fluid through the irrigation fluid outlet.

15 Claims, 16 Drawing Sheets

(51) Int. Cl.
*A61F 9/007* (2006.01)
*A61M 39/24* (2006.01)

(52) U.S. Cl.
CPC ........ *A61M 1/0064* (2013.01); *A61M 1/0086* (2014.02); *A61M 2039/244* (2013.01); *A61M 2039/2426* (2013.01); *A61M 2210/0612* (2013.01)

(56) References Cited

U.S. PATENT DOCUMENTS

| | | |
|---|---|---|
| 3,624,907 A | 12/1971 | Brass et al. |
| 3,745,645 A | 7/1973 | Kurth et al. |
| 3,745,655 A | 7/1973 | Malmin |
| 3,749,090 A | 7/1973 | Stewart |
| 3,805,787 A | 4/1974 | Banko |
| 3,807,048 A | 4/1974 | Malmin |
| 3,848,748 A | 11/1974 | Ceccarelli |
| 3,871,099 A | 3/1975 | Kahn |
| 3,949,748 A | 4/1976 | Malmin |
| 3,994,297 A | 11/1976 | Kopf |
| 4,014,333 A | 3/1977 | McIntyre |
| 4,016,879 A | 4/1977 | Mellor |
| 4,047,532 A | 9/1977 | Phillips et al. |
| 4,099,528 A | 7/1978 | Sorenson et al. |
| 4,204,328 A | 5/1980 | Kutner |
| 4,386,927 A | 6/1983 | Eichenbaum |
| 4,436,125 A | 3/1984 | Blenkush |
| 4,445,509 A | 5/1984 | Auth |
| 4,461,281 A | 7/1984 | Carson |
| 4,487,600 A | 12/1984 | Brownlie et al. |
| 4,500,118 A | 2/1985 | Blenkush |
| 4,519,385 A | 5/1985 | Atkinson et al. |
| 4,531,943 A | 7/1985 | Van Tassel et al. |
| 4,553,957 A | 11/1985 | Williams et al. |
| 4,573,979 A | 3/1986 | Blake |
| 4,578,059 A | 3/1986 | Fabricant et al. |
| 4,630,847 A | 12/1986 | Blenkush |
| 4,652,255 A | 3/1987 | Martinez |
| 4,671,790 A | 6/1987 | Nishi |
| 4,710,180 A | 12/1987 | Johnson |
| 4,717,387 A | 1/1988 | Inoue et al. |
| 4,813,926 A | 3/1989 | Kerwin |
| 4,878,900 A | 11/1989 | Sundt |
| 4,897,079 A | 1/1990 | Zaleski et al. |
| 4,903,995 A | 2/1990 | Blenkush et al. |
| 4,904,238 A | 2/1990 | Williams |
| 4,921,482 A | 5/1990 | Hammerslag et al. |
| 4,928,859 A | 5/1990 | Krahn et al. |
| 4,934,655 A | 6/1990 | Blenkush et al. |
| 4,941,872 A | 7/1990 | Felix et al. |
| 4,983,160 A | 1/1991 | Steppe et al. |
| 4,998,916 A | 3/1991 | Hammerslag et al. |
| 4,998,923 A | 3/1991 | Samson et al. |
| 5,033,777 A | 7/1991 | Blenkush |
| 5,037,391 A | 8/1991 | Hammerslag et al. |
| 5,052,725 A | 10/1991 | Meyer et al. |
| 5,084,009 A | 1/1992 | Mackool |
| 5,084,012 A | 1/1992 | Kelman |
| 5,104,158 A | 4/1992 | Meyer et al. |
| 5,106,381 A | 4/1992 | Chikama |
| 5,108,368 A | 4/1992 | Hammerslag et al. |
| 5,123,906 A | 6/1992 | Kelman |
| 5,131,382 A | 7/1992 | Meyer |
| 5,133,159 A | 7/1992 | Nelson |
| 5,151,084 A | 9/1992 | Khek |
| 5,154,696 A | 10/1992 | Shearing |
| 5,176,126 A | 1/1993 | Chikama |
| 5,178,303 A | 1/1993 | Blenkush et al. |
| 5,178,605 A | 1/1993 | Imonti |
| 5,203,772 A | 4/1993 | Hammerslag et al. |
| 5,217,465 A | 6/1993 | Steppe |
| 5,242,449 A | 9/1993 | Zaleski |
| 5,261,883 A | 11/1993 | Hood et al. |
| 5,286,256 A | 2/1994 | Mackool |
| 5,290,892 A | 3/1994 | Namdaran et al. |
| 5,292,310 A | 3/1994 | Yoon |
| 5,308,324 A | 5/1994 | Hammerslag et al. |
| 5,316,041 A | 5/1994 | Ramacier, Jr. et al. |
| 5,328,456 A | 7/1994 | Horiguchi et al. |
| 5,353,836 A | 10/1994 | deCler et al. |
| 5,354,265 A | 10/1994 | Mackool |
| 5,354,291 A | 10/1994 | Bales et al. |
| 5,358,507 A | 10/1994 | Daily |
| 5,364,405 A | 11/1994 | Zaleski |
| 5,372,587 A | 12/1994 | Hammerslag et al. |
| 5,378,234 A | 1/1995 | Hammerslag et al. |
| 5,381,782 A | 1/1995 | DeLaRama et al. |
| D357,307 S | 4/1995 | Ramacier, Jr. et al. |
| 5,403,901 A | 4/1995 | Namdaran et al. |
| 5,413,556 A | 5/1995 | Whittingham |
| 5,421,955 A | 6/1995 | Lau et al. |
| 5,433,746 A | 7/1995 | Namdaran et al. |
| 5,441,496 A | 8/1995 | Easley et al. |
| 5,451,229 A | 9/1995 | Geuder et al. |
| 5,453,087 A | 9/1995 | Malinowski |
| 5,454,827 A | 10/1995 | Aust et al. |
| 5,514,086 A | 5/1996 | Parisi et al. |
| 5,522,826 A | 6/1996 | Daily |
| 5,531,744 A | 7/1996 | Nardella et al. |
| 5,603,710 A | 2/1997 | Easley et al. |
| 5,645,530 A | 7/1997 | Boukhny et al. |
| 5,651,783 A | 7/1997 | Reynard |
| 5,702,270 A | 12/1997 | Casica et al. |
| 5,718,677 A | 2/1998 | Capetan et al. |
| 5,746,713 A | 5/1998 | Hood et al. |
| 5,749,893 A | 5/1998 | Vidal et al. |
| 5,785,647 A | 7/1998 | Tompkins et al. |
| 5,792,098 A | 8/1998 | Felix et al. |
| 5,830,192 A | 11/1998 | Van Voorhis |
| 5,836,926 A | 11/1998 | Peterson et al. |
| 5,845,943 A | 12/1998 | Ramacier, Jr. et al. |
| 5,851,212 A | 12/1998 | Zirps et al. |
| 5,873,851 A | 2/1999 | Nilsson |
| 5,876,379 A | 3/1999 | Beauvais et al. |
| 5,897,523 A | 4/1999 | Wright et al. |
| 5,899,914 A | 5/1999 | Zirps et al. |
| 5,911,403 A | 6/1999 | deCler et al. |
| 5,919,157 A | 7/1999 | Strukel |
| 5,921,998 A | 7/1999 | Tano et al. |
| 5,938,244 A | 8/1999 | Meyer |
| 5,938,678 A | 8/1999 | Zirps et al. |
| 5,941,887 A * | 8/1999 | Steen ................. A61F 9/00745 604/22 |
| 5,957,928 A | 9/1999 | Kirwan, Jr. |
| 5,984,889 A | 11/1999 | Christ et al. |
| 5,989,209 A | 11/1999 | Barrett |
| 6,007,513 A | 12/1999 | Anis et al. |
| 6,007,555 A | 12/1999 | Devine |
| 6,010,054 A | 1/2000 | Johnson et al. |
| 6,013,049 A | 1/2000 | Rockley et al. |
| 6,024,124 A | 2/2000 | Braun et al. |
| 6,048,339 A | 4/2000 | Zirps et al. |
| 6,053,907 A | 4/2000 | Zirps |
| 6,068,641 A | 5/2000 | Varsseveld |
| 6,077,287 A | 6/2000 | Taylor et al. |
| 6,117,151 A | 9/2000 | Urich et al. |
| 6,132,426 A | 10/2000 | Kroll |
| 6,161,578 A | 12/2000 | Braun et al. |
| 6,165,168 A * | 12/2000 | Russo ................. A61M 39/045 604/247 |
| 6,179,807 B1 | 1/2001 | Henniges et al. |
| 6,183,433 B1 | 2/2001 | Bays |
| 6,231,089 B1 | 5/2001 | DeCler et al. |
| 6,234,993 B1 | 5/2001 | Terpilowski et al. |
| 6,241,700 B1 | 6/2001 | Leukanech |
| 6,299,591 B1 | 10/2001 | Banko |
| 6,340,355 B1 | 1/2002 | Barrett |
| 6,382,593 B1 | 5/2002 | deCler et al. |
| 6,398,759 B1 | 6/2002 | Sussman et al. |
| 6,423,074 B1 | 7/2002 | Chen |
| 6,428,501 B1 | 8/2002 | Reynard |
| 6,491,670 B1 | 12/2002 | Toth et al. |
| 6,520,929 B2 | 2/2003 | Zaleski |

(56) References Cited

U.S. PATENT DOCUMENTS

| | | |
|---|---|---|
| 6,544,254 B1 | 4/2003 | Bath |
| 6,554,842 B2 | 4/2003 | Heuser et al. |
| 6,575,989 B1 | 6/2003 | Scheller et al. |
| 6,579,270 B2 | 6/2003 | Sussman et al. |
| 6,592,541 B1 | 7/2003 | Kurwa |
| 6,623,477 B1 | 9/2003 | Elbrecht et al. |
| 6,626,419 B2 | 9/2003 | deCler et al. |
| 6,645,218 B1 | 11/2003 | Cassidy et al. |
| 6,649,829 B2 | 11/2003 | Garber et al. |
| 6,656,195 B2 | 12/2003 | Peters et al. |
| 6,705,591 B2 | 3/2004 | deCler |
| 6,830,555 B2 | 12/2004 | Rockley et al. |
| 6,848,602 B2 | 2/2005 | deCler et al. |
| 6,852,092 B2 | 2/2005 | Kadziauskas et al. |
| 6,852,093 B1 | 2/2005 | Boukhny |
| 6,871,669 B2 | 3/2005 | Meyer et al. |
| 6,893,414 B2 | 5/2005 | Goble et al. |
| 6,902,144 B2 | 6/2005 | deCler |
| 6,902,558 B2 | 6/2005 | Laks |
| 6,916,007 B2 | 7/2005 | DeCler et al. |
| 6,932,788 B2 | 8/2005 | Kamiyama et al. |
| 6,962,275 B2 | 11/2005 | deCler et al. |
| 6,978,800 B2 | 12/2005 | deCler et al. |
| 7,014,629 B2 | 3/2006 | Mackool |
| RE39,152 E | 6/2006 | Aust et al. |
| 7,066,923 B2 | 6/2006 | Tjia |
| 7,080,665 B2 | 7/2006 | Whall |
| 7,094,229 B2 | 8/2006 | Boukhny et al. |
| 7,303,566 B2 | 12/2007 | Kishimoto et al. |
| 7,329,261 B2 | 2/2008 | Perkins |
| 7,352,771 B2 | 4/2008 | Garber |
| 7,357,779 B2 | 4/2008 | Barrett |
| 7,394,375 B2 | 7/2008 | Johnson |
| 7,434,842 B2 | 10/2008 | Schmidt |
| 7,469,472 B2 | 12/2008 | deCler et al. |
| 7,546,857 B2 | 6/2009 | Chadbourne et al. |
| D602,128 S | 10/2009 | Williams et al. |
| 7,631,660 B2 | 12/2009 | deCler et al. |
| 7,647,954 B2 | 1/2010 | Garber et al. |
| D612,019 S | 3/2010 | Williams et al. |
| 7,695,020 B2 | 4/2010 | Schmidt |
| 7,704,244 B2 | 4/2010 | Boukhny et al. |
| 7,708,025 B2 | 5/2010 | Johnson |
| 7,841,357 B2 | 11/2010 | Rankin |
| 7,883,521 B2 | 2/2011 | Rockley et al. |
| 7,954,374 B2 | 6/2011 | Rankin |
| 7,954,515 B2 | 6/2011 | Gerst |
| 7,967,775 B2 | 6/2011 | Hong |
| D649,938 S | 12/2011 | Erickson et al. |
| D649,939 S | 12/2011 | Erickson et al. |
| 8,162,919 B2 | 4/2012 | Cull et al. |
| 8,454,551 B2 | 6/2013 | Allen et al. |
| 8,454,625 B2 | 6/2013 | Yoshida et al. |
| 8,475,403 B2 | 7/2013 | Melsheimer et al. |
| 8,491,016 B2 | 7/2013 | Williams et al. |
| 8,568,396 B2 | 10/2013 | Bourne |
| 8,784,361 B2 | 7/2014 | Lane |
| 2001/0037082 A1 | 11/2001 | Kamiyama et al. |
| 2002/0011730 A1 | 1/2002 | Stickan |
| 2002/0170731 A1 | 11/2002 | Garber et al. |
| 2002/0190453 A1 | 12/2002 | Wilhelm et al. |
| 2003/0004455 A1 | 1/2003 | Kadziauskas et al. |
| 2003/0069594 A1 | 4/2003 | Rockley et al. |
| 2003/0199883 A1 | 10/2003 | Laks |
| 2003/0208218 A1 | 11/2003 | Kadziauskas et al. |
| 2004/0030281 A1 | 2/2004 | Goble et al. |
| 2004/0068270 A1 | 4/2004 | Allred, III |
| 2004/0089080 A1 | 5/2004 | Kadziauskas et al. |
| 2004/0092921 A1 | 5/2004 | Kadziauskas et al. |
| 2004/0153093 A1 | 8/2004 | Donovan |
| 2004/0153111 A1 | 8/2004 | Hosoada |
| 2005/0049547 A1 | 3/2005 | Anspach et al. |
| 2005/0054971 A1 | 3/2005 | Steen et al. |
| 2005/0154434 A1 | 7/2005 | Simon et al. |
| 2005/0159758 A1 | 7/2005 | Laks |
| 2005/0171469 A1 | 8/2005 | Cunningham |
| 2005/0234473 A1 | 10/2005 | Zacharias |
| 2005/0237241 A1 | 10/2005 | Garber et al. |
| 2005/0245911 A1 | 11/2005 | Wright et al. |
| 2005/0256462 A1 | 11/2005 | Underwood |
| 2005/0273063 A1 | 12/2005 | Hoell et al. |
| 2005/0277898 A1 | 12/2005 | Dimalanta et al. |
| 2005/0288650 A1 | 12/2005 | Boukhny et al. |
| 2006/0036215 A1 | 2/2006 | Boukhny |
| 2006/0047241 A1 | 3/2006 | Boukhny |
| 2006/0048849 A1 | 3/2006 | deCler |
| 2006/0057538 A1 | 3/2006 | Hoeffleur |
| 2006/0116703 A1 | 6/2006 | Glaser |
| 2006/0135974 A1 | 6/2006 | Perkins |
| 2006/0212038 A1 | 9/2006 | Boukhny |
| 2007/0025811 A1 | 2/2007 | Wilhelm |
| 2007/0100277 A1 | 5/2007 | Shippert |
| 2007/0179512 A1 | 8/2007 | Olsen et al. |
| 2007/0244425 A1 | 10/2007 | Pond |
| 2007/0260173 A1 | 11/2007 | Boukhny et al. |
| 2007/0278786 A1 | 12/2007 | Mezhinsky et al. |
| 2007/0282348 A1 | 12/2007 | Lumpkin |
| 2008/0011785 A1 | 1/2008 | Braun et al. |
| 2008/0167604 A1 | 7/2008 | Hong |
| 2009/0062751 A1 | 3/2009 | Newman, Jr. |
| 2009/0170052 A1 | 7/2009 | Borczyk |
| 2009/0188575 A1 | 7/2009 | Williams et al. |
| 2010/0019487 A1 | 1/2010 | deCler et al. |
| 2010/0121260 A1 | 5/2010 | Ghannoum et al. |
| 2010/0295295 A1 | 11/2010 | Schmidt |
| 2011/0062701 A1 | 3/2011 | Downs et al. |
| 2011/0137231 A1 | 6/2011 | Sorensen et al. |
| 2011/0144567 A1 | 6/2011 | Sorensen et al. |
| 2012/0035532 A1 | 2/2012 | Melsheimer et al. |
| 2012/0143125 A1 | 6/2012 | Lane |
| 2012/0161051 A1 | 6/2012 | Williams et al. |
| 2012/0179052 A1 | 7/2012 | Wilhelm et al. |
| 2013/0092271 A1 | 4/2013 | Downs et al. |
| 2013/0165850 A1* | 6/2013 | Schaller ............. A61M 3/0283 604/44 |
| 2013/0207380 A1 | 8/2013 | Williams et al. |
| 2014/0163455 A1 | 6/2014 | Wilson et al. |
| 2014/0276377 A1* | 9/2014 | Chang ................. A61M 1/0084 604/35 |

FOREIGN PATENT DOCUMENTS

| | | |
|---|---|---|
| CN | 102245222 A | 11/2011 |
| CN | 104114203 A | 10/2014 |
| DE | 3822011 A1 | 1/1990 |
| DE | 3822011 C2 | 4/1994 |
| DE | 4313245 | 3/1997 |
| DE | 19700809 | 7/1998 |
| EP | 0778039 A1 | 6/1997 |
| EP | 0864310 A1 | 9/1998 |
| EP | 0997108 A2 | 5/2000 |
| EP | 1095641 A1 | 5/2001 |
| EP | 1371347 A2 | 12/2003 |
| EP | 1607076 A1 | 12/2005 |
| EP | 1607077 A1 | 12/2005 |
| EP | 1820474 A2 | 8/2007 |
| EP | 1852095 A1 | 11/2007 |
| FR | 2713492 | 6/1995 |
| JP | 04176457 A | 6/1992 |
| JP | H09-313522 | 12/1997 |
| JP | 10071166 | 3/1998 |
| JP | 2002512845 A | 5/2002 |
| JP | 2006006953 A | 1/2006 |
| JP | 4429164 B2 | 3/2010 |
| JP | 2014504908 A | 2/2014 |
| RU | 285170 | 10/1970 |
| WO | 92/10139 A1 | 6/1992 |
| WO | 94/23773 A1 | 10/1994 |
| WO | 98/07398 A1 | 2/1998 |
| WO | 99/11313 A1 | 3/1999 |
| WO | 9915120 A1 | 4/1999 |
| WO | 0009925 A1 | 2/2000 |
| WO | 0119255 A1 | 3/2001 |
| WO | 0192769 A2 | 12/2001 |

(56) References Cited

FOREIGN PATENT DOCUMENTS

| WO | 02/28449 A2 | 4/2002 |
|---|---|---|
| WO | 2006/018579 A2 | 2/2006 |
| WO | 2007/006466 A1 | 1/2007 |
| WO | 2007011302 A1 | 1/2007 |
| WO | 2010/056448 A1 | 5/2010 |
| WO | 2011031448 A2 | 3/2011 |
| WO | 2012/078319 A1 | 6/2012 |
| WO | 2012088463 A1 | 6/2012 |
| WO | 2013126766 A2 | 8/2013 |
| WO | 2014/197161 A1 | 12/2014 |

OTHER PUBLICATIONS

International Searching Authority, Written Opinion of the International Searching Authority, PCT/US2014/037293, Sep. 26, 2014, 4 pages.
Dr. Ulrich Naumann, Notice of Opposition and EPO Communication, Sep. 23, 2010, 44 pages.
Alcon Silicone I/A Tip, Alcon, Inc., dated Jan. 1, 2007, CAT281, 2 pgs.
EP1852095; Opposition Letter dated Sep. 27, 2012—English translation.
EP1852095; Opposition Submission; Letter dated Sep. 26, 2011—English translation.
EP1852095; Prosecution History dated Apr. 25, 2007, Opposition filed.
Extended European Search Report issued for Patent Application No. EP 12860162, dated Aug. 26, 2014, 7 pages.
International Search Report and Written Opinion for PCT/US2009/060315, 10 pages, dated Jan. 12, 2010.
International Search Report and Written Opinion for PCT/US2011/060751, 7 pages, dated Feb. 6, 2012.
International Search Report and Written Opinion for PCT/US2012/069646, 8 pages, dated Mar. 5, 2013.
Alcon Cataract Product Catalog, 2008/2009, pp. 17-33 (along with front and back covers), copyright Jun. 2008.
Lane, Stephen, Prosecution History, U.S. Appl. No. 12/962,082, filed Dec. 7, 2010, 940 pages.
Schaller, Philipp, Prosecution History, U.S. Appl. No. 13/686,430, filed Nov. 27, 2012, 1033 pages.
Chang, David F. "Transitioning to Bimanual Microincisional Phacoemulsification", Cataract & Refractive Surgery Today, Sep. 2004, pp. 68-71.
Packer, Mark, et. al. "Bimanual Microincisional Phacoemulsification", Cataract & Refractive Surgery Today, Nov./Dec. 2005, pp. 60-62.
Araujo-Gomes, Fernando, "Solving the Pitfalls of Bimanual Phacoemulsification—Oval Instruments Do Save Energy", European Ophthalmic Review, Touch Briefings, 2007, pp. 39-41.
Wang, Yujuan et al. "Comparison of bimanual and micro-coaxial phacoemulsification with torsional ultrasound" by Acta Ophthalmologica 2012.
Lou, MD, PhD, Bet al. "Residual Lens Cortex Material: Potential Risk Factor for Endophthalmitis after Phacoemulsification Cataract Surgery," Journal of Cataract Refractive Surgery, vol. 39, Feb. 2013, 8 pages.

* cited by examiner

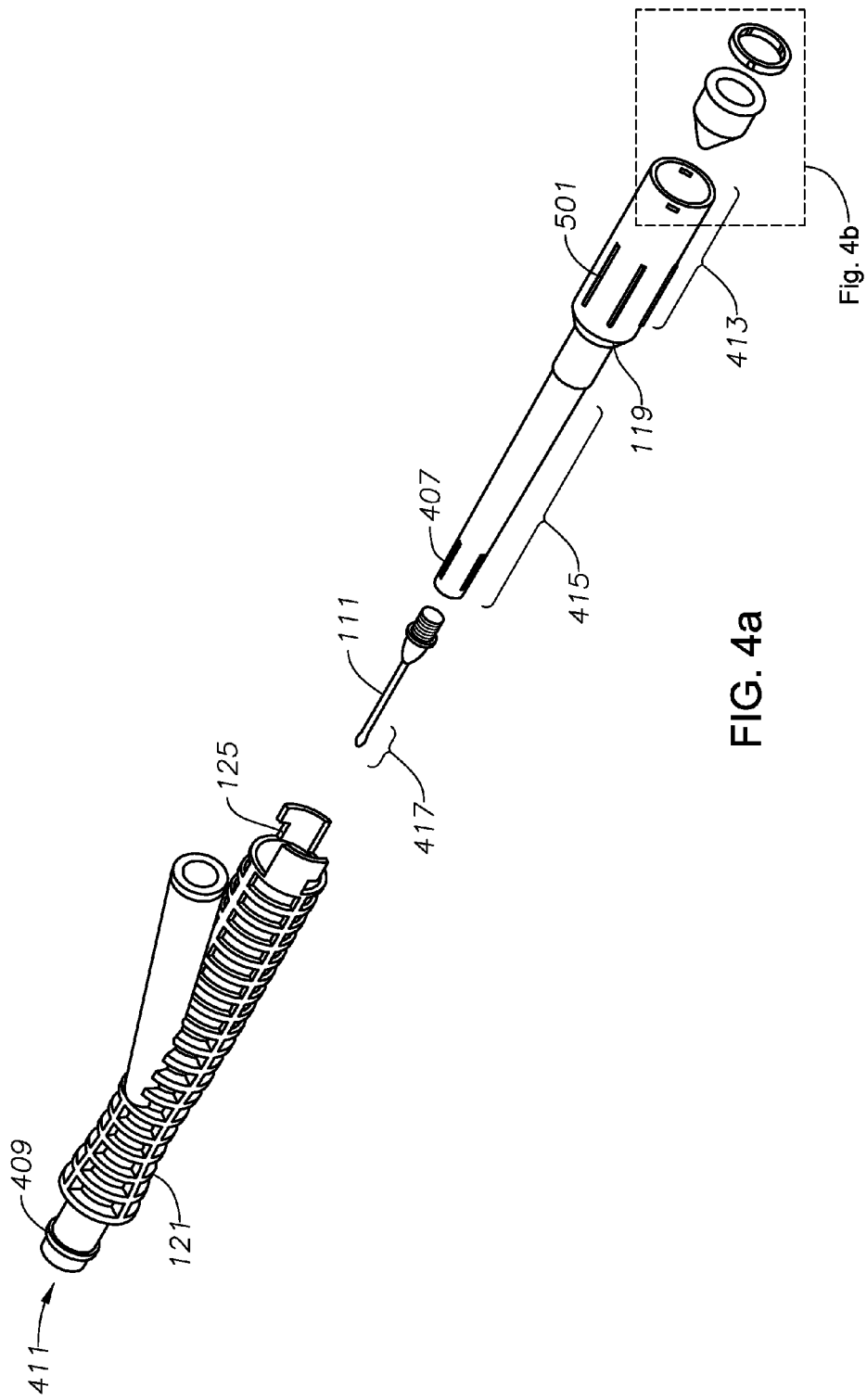

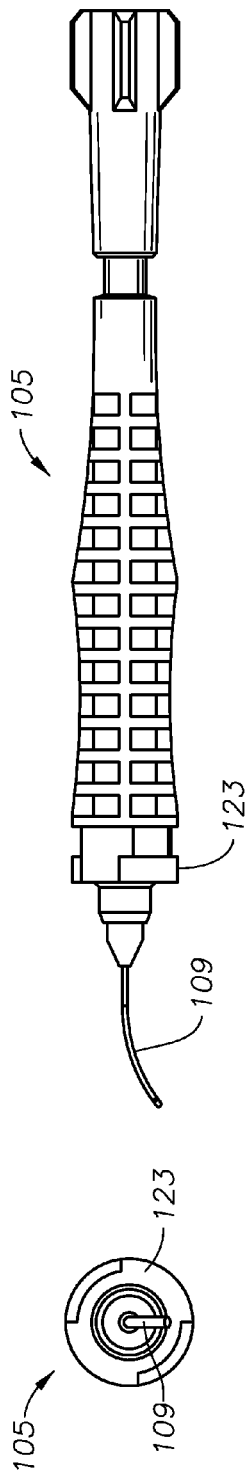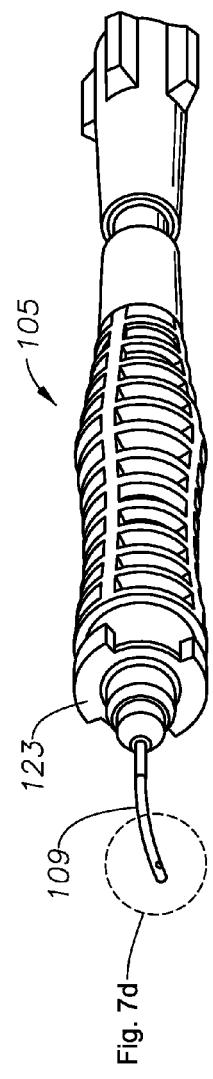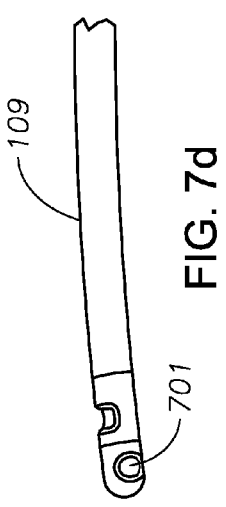

TRANSFORMER IRRIGATION/ASPIRATION DEVICE

PRIORITY CLAIM

This application claims the benefit of priority of U.S. Provisional Patent Application Ser. No. 61/831,665 titled "Transformer Irrigation/Aspiration Device", filed on Jun. 6, 2013, whose inventors are G. Lamar Kirchhevel and Charles Kittridge Beauvias, which is hereby incorporated by reference in its entirety as though fully and completely set forth herein.

FIELD OF THE INVENTION

The present invention generally pertains to surgical devices. More particularly, but not by way of limitation, the present invention pertains to irrigation/aspiration devices.

DESCRIPTION OF THE RELATED ART

Cataract surgery may include removing a cloudy natural lens and surrounding cortex and replacing it with a clear artificial lens. Removing the natural lens may include using a powered, irrigating, vibrating tip (for lens phacoemulsification and removal) followed by an irrigating and aspirating tip for cortex removal.

Predicate cortex removal devices include coaxial and bimanual devices. The one-handed, coaxial device may include an aspirating tip surrounded by an irrigating sleeve. The two-handed, bimanual devices may include two separate instruments—one providing an irrigation cannula and the other an aspiration cannula. The coaxial device may include two tubing connections, one to provide irrigation fluid and one for aspiration vacuum while the bimanual devices may include a tubing connection for irrigation fluid on the irrigation cannula device and a separate tubing connection for vacuum on the aspiration cannula device.

SUMMARY

In various embodiments, a cannula device may be transformable between a coaxial mode and a bimanual mode by coupling (for coaxial) and de-coupling (for bimanual) an aspiration handpiece portion and an irrigation handpiece portion making up the cannula device. In some embodiments, the irrigation handpiece portion and the aspiration handpiece portion may include interlocking elements for releasably coupling the distal end of the aspiration handpiece portion to the proximal end of the irrigation handpiece portion.

In coaxial mode, the aspiration handpiece portion may be coupled to the irrigation handpiece portion such that fluid is aspirated in a main incision by a first aspiration tip, on the irrigation handpiece portion, and then aspirated through a second aspiration tip, on the aspiration handpiece portion (the second aspiration tip being located at least partially inside the irrigation handpiece portion in fluid communication with the first aspiration tip). In coaxial mode, irrigation fluid may be provided through an irrigation fluid outlet on the irrigation handpiece portion. In some embodiments, the irrigation fluid outlet may be a port in an irrigation sleeve coupled to a distal end of the irrigation handpiece portion. The irrigation sleeve may at least partially surround the first aspiration tip extending from the irrigation handpiece portion.

In bimanual mode, the aspiration handpiece portion may be decoupled from the irrigation handpiece portion to provide aspiration through the second aspiration tip (placed into a second incision) while the irrigation handpiece portion continues to provide irrigation fluid through the irrigation fluid outlet (in the main incision). In bimanual mode, the irrigation handpiece portion may not provide aspiration through the first aspiration tip.

In some embodiments, the cannula device may also include a seal in a proximal end of the irrigation handpiece portion that is configured to receive the second aspiration tip when the aspiration handpiece portion is coupled to the irrigation handpiece portion. In some embodiments, the seal is cone-shaped and configured to fit within a distal portion of the irrigation handpiece portion such that the walls of the seal press against the inner wall of the irrigation handpiece portion to inhibit fluid flow between the walls of the seal and the inner wall of the irrigation handpiece portion. In some embodiments, the seal may include an O-ring configured to press against the inner wall of the irrigation handpiece portion to inhibit fluid flow between the O-ring and the inner wall of the irrigation handpiece portion. In some embodiments, the seal may be configured to inhibit aspiration fluid flow out of irrigation handpiece portion when the aspiration handpiece portion is removed from the irrigation handpiece portion. In some embodiments, the cannula device may also include a retainer to retain the seal in the irrigation handpiece portion as the aspiration handpiece portion is inserted and withdrawn from the irrigation handpiece portion.

In some embodiments, an aspiration tip of an aspiration handpiece portion may be inserted into a seal in an irrigation handpiece portion to place the aspiration tip of the aspiration handpiece portion in fluid communication with an aspiration pathway of the irrigation handpiece portion such that fluid entering an aspiration tip on the irrigation handpiece portion passes through the interior of the irrigation handpiece portion, into the aspiration tip of the aspiration handpiece portion and then out of the aspiration handpiece portion. Once the tip is inserted, the aspiration handpiece portion may be coupled to the irrigation handpiece portion to form a coaxial handpiece. Coupling the aspiration handpiece portion to the irrigation handpiece portion may include twisting together interlocking elements on the aspiration handpiece portion and the irrigation handpiece portion. After coupling, the coaxial handpiece may then provide aspiration through the aspiration tip on the irrigation handpiece portion and irrigation fluid through an irrigation fluid outlet on the irrigation handpiece portion. To put the cannula device in bimanual mode, the aspiration handpiece portion may be decoupled from the irrigation handpiece portion and the aspiration tip of the aspiration handpiece portion may be withdrawn from the seal in the irrigation handpiece portion to form two separate handpieces. Irrigation fluid may then be provided through the irrigation fluid outlet on the irrigation handpiece portion while aspiration is provided through the aspiration tip on the aspiration handpiece portion. In some embodiments, providing irrigation fluid through the irrigation fluid outlet may include providing irrigation fluid through a port in an irrigation sleeve coupled to a distal end of the irrigation handpiece portion (the irrigation sleeve may at least partially surround the aspiration tip on the irrigation handpiece portion).

BRIEF DESCRIPTION OF THE DRAWINGS

For a more complete understanding of the present invention, reference is made to the following description taken in conjunction with the accompanying drawings in which:

FIGS. 4a-d illustrate insertion of the check valve and snap-in retainer into an aspiration tube, according to an embodiment;

FIGS. 7a-d illustrate various views of the aspiration handpiece portion, according to an embodiment;

It is to be understood that both the foregoing general description and the following detailed description are exemplary and explanatory only and are intended to provide a further explanation of the present invention as claimed.

DETAILED DESCRIPTION OF THE EMBODIMENTS

Figure 1A:
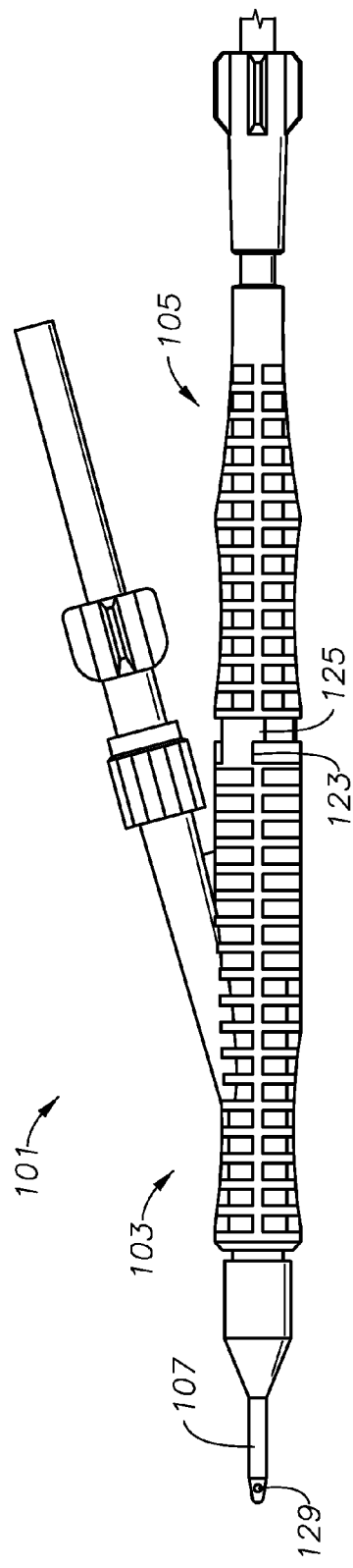
FIGS. 1a-c illustrate the cannula device in coaxial mode, according to an embodiment.
Figure 1B:
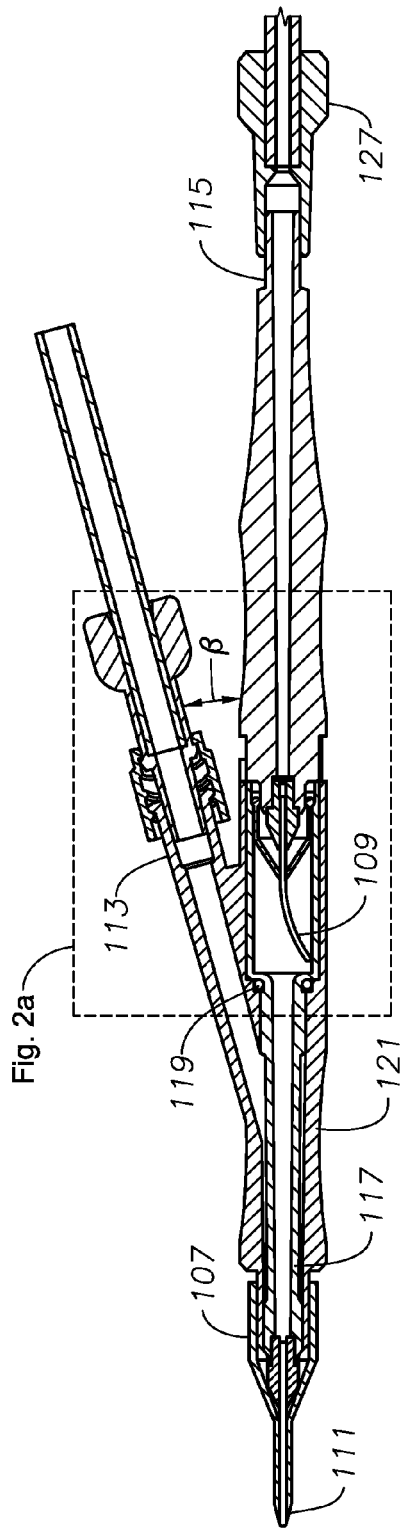
Figure 1C:
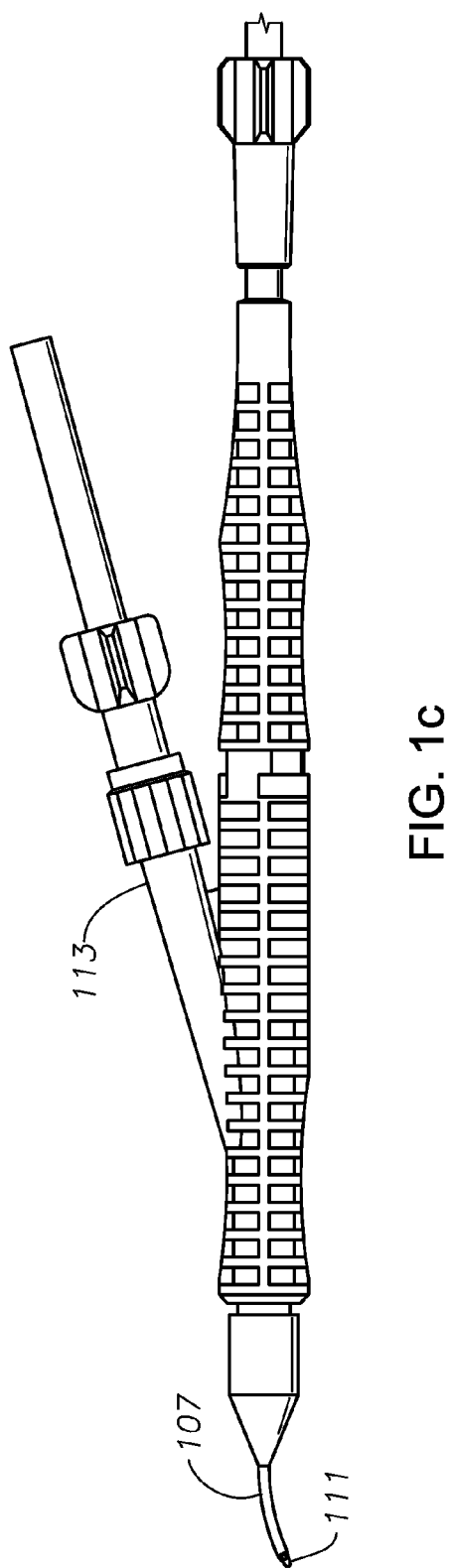
Figure 1D:
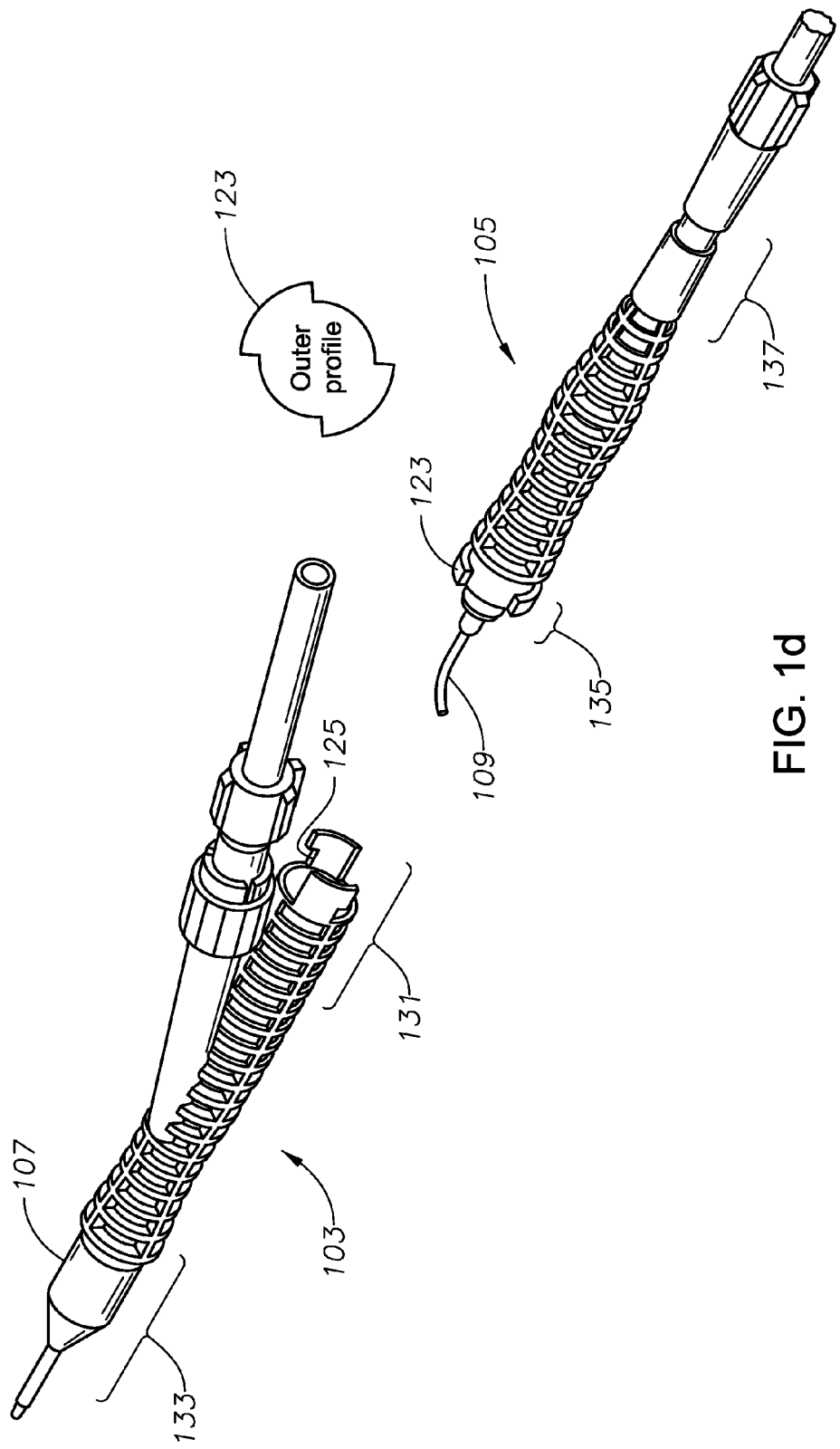
FIG. 1d illustrates the cannula device in bimanual mode, according to an embodiment.

In some embodiments, an ophthalmic irrigation/aspiration cannula device 101 may support both a coaxial mode (one-handed) and a bimanual mode (two-handed). Cannula device 101 may be configured to transform between a single coaxial handpiece (as shown in FIGS. 1a-c) and separated bimanual handpieces (as shown in FIG. 1d). In both modes, irrigation fluid may be provided (e.g., into a first incision in an eye) through irrigation fluid outlet port 129 in sleeve 107 at distal end 133 of irrigation handpiece portion 103. In coaxial mode, aspiration may be provided through first aspiration tip 111 in sleeve 107, while in bimanual mode, aspiration may be provided by second aspiration tip 109 on a separated aspiration handpiece portion 105 (e.g., inserted into a second incision in the eye). In some embodiments, aspiration may not be provided through first aspiration tip 111 while in bimanual mode. When cannula device 101 is assembled for coaxial mode, the aspiration pathway may be through both the first and second aspiration tips in series, with first aspiration tip 111 inside sleeve 107 and second aspiration tip 109 inside the cannula device handle (formed at least partially from outer irrigation handpiece casing 121). Fluid may initially enter a hole in distal end 417 of first aspiration tip 111, flow through aspiration tube 117, be aspirated by second aspiration tip 109 inside the handle, and then exit cannula device 101 through connector 115 on proximal end 137 of aspiration handpiece portion 105.

In some embodiments, for bi-manual operation, cannula device 101 may be separated into the two handpieces (i.e., irrigation handpiece 103 and aspiration handpiece 105) by uncoupling aspiration handpiece portion 105 from irrigation handpiece portion 103 and removing aspiration handpiece portion 105 from irrigation handpiece portion 103. For example, as seen in FIG. 1d, aspiration handpiece portion 105 may be twisted to disengage tab 123 on aspiration handpiece portion 105 from slot 125 in irrigation handpiece portion 103 and then axially pulled to separate aspiration handpiece portion 105 from irrigation handpiece portion 103. In some embodiments, cannula device 101 may be transformed into the two separate handpieces without adding, removing or changing tubing connections or removing sleeve 107. With aspiration handpiece portion 105 separated from irrigation handpiece portion 103, second aspiration tip 109 may then be inserted through a secondary incision in the eye for aspiration (e.g. to enable removal of sub-incision cortex). In some embodiments, cannula device 101 may be transformed back into a unitary handpiece for coaxial operation by coupling aspiration handpiece portion 105 to irrigation handpiece portion 103. For example, second aspiration tip 109 of aspiration handpiece portion 105 may be inserted into proximal end 131 of irrigation handpiece portion 103, and then aspiration handpiece portion 105 may be twisted to engage tab 123 with slot 125 to lock aspiration handpiece portion 105 to irrigation handpiece portion 103. In some embodiments, tab 123 and slot 125 may be dimensioned to provide a friction fit when aspiration handpiece portion 105 is twisted onto irrigation handpiece portion 103 to engage the tab 123 and slot 125. Other engagement mechanisms are also contemplated (e.g., tab and slot snap configuration, tube in tube friction fit, etc.)

Figure 2A:
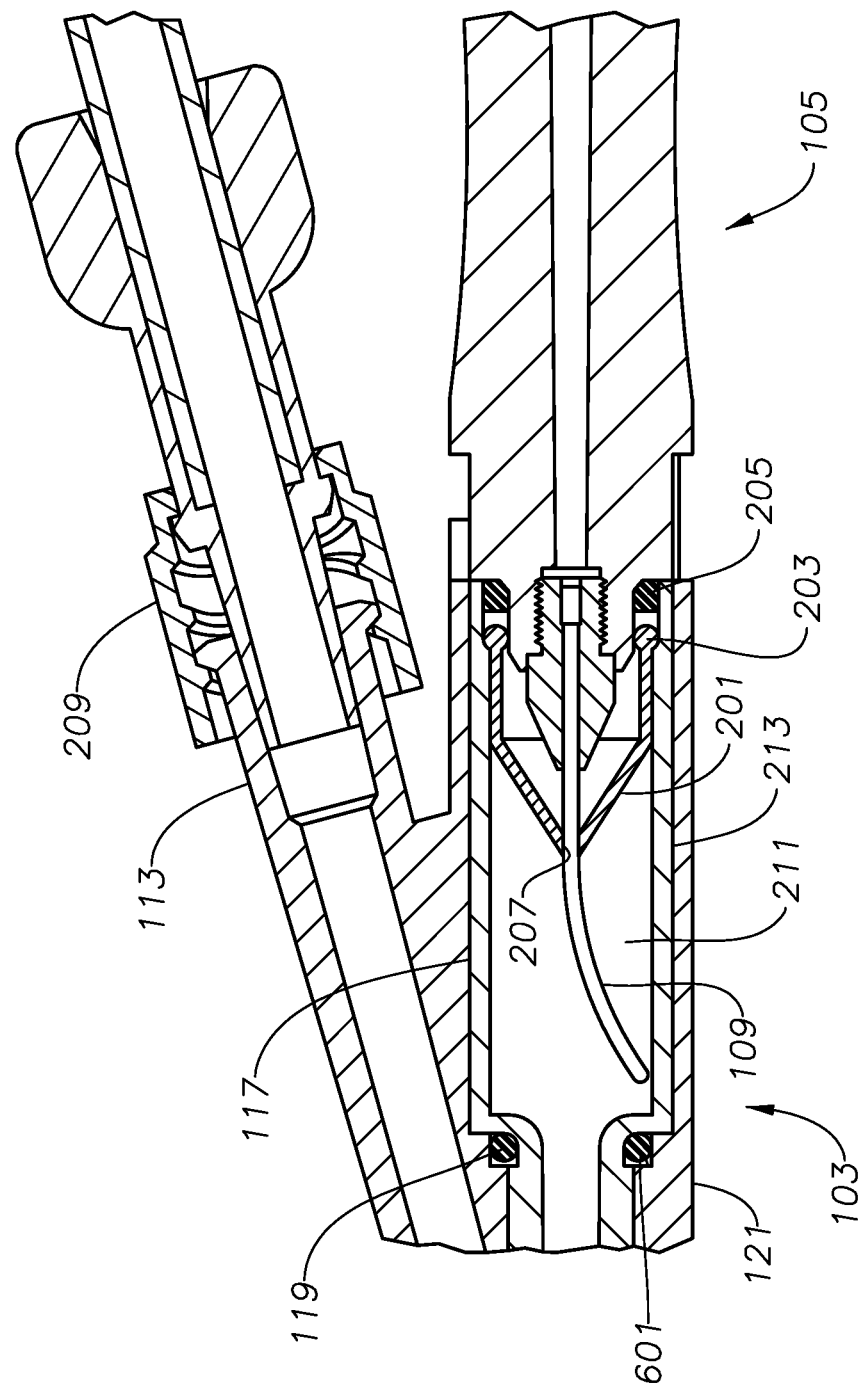
FIG. 2a illustrates a cross section of the coupling portion of the irrigation handpiece portion, according to an embodiment.

As seen in FIG. 2a, in some embodiments, check valve 201 in irrigation handpiece portion 103 of cannula device 101 may inhibit fluid from exiting irrigation handpiece portion 103 when irrigation handpiece portion 103 and aspiration handpiece portion 105 are separated, but may allow fluid communication through tip 109 when irrigation handpiece portion 103 and aspiration handpiece portion 105 are coupled together. In some embodiments, O-ring 203 may further prevent aspiration fluid from flowing around check valve 201 between irrigation handpiece portion 103 and aspiration handpiece portion 105 when irrigation handpiece portion 103 and aspiration handpiece portion 105 are coupled together. In some embodiments, the check valve 201 and O-ring 203 may be elastomeric (e.g., made of a polymer). Other materials for the check valve and O-ring are also contemplated. In some embodiments, shallow grooves 213 in the inner wall of the outer irrigation handpiece casing 121 (e.g., see FIG. 2a) may receive corresponding ribs 501 (see FIG. 5) on aspiration tube 117 for alignment and retention of aspiration tube 117 inside outer irrigation handpiece casing 121 and to inhibit rotation of aspiration tube 117 inside outer irrigation handpiece casing 121. In some embodiments, aspiration tube 117 may be smooth and not include ribs 501. In some embodiments, the inner wall of the outer irrigation handpiece casing 121 may be smooth (i.e., not include shallow grooves 213) and aspiration tube 117 may have a friction fit with the inner walls of irrigation handpiece casing 121. For example, ribs 501 on aspiration tube 117 may be configured to crush against the inner walls of irrigation handpiece casing 121 as aspiration tube 117 is inserted therein to provide a secure friction fit between aspiration tube 117 and irrigation handpiece casing 121.

Figure 2B:
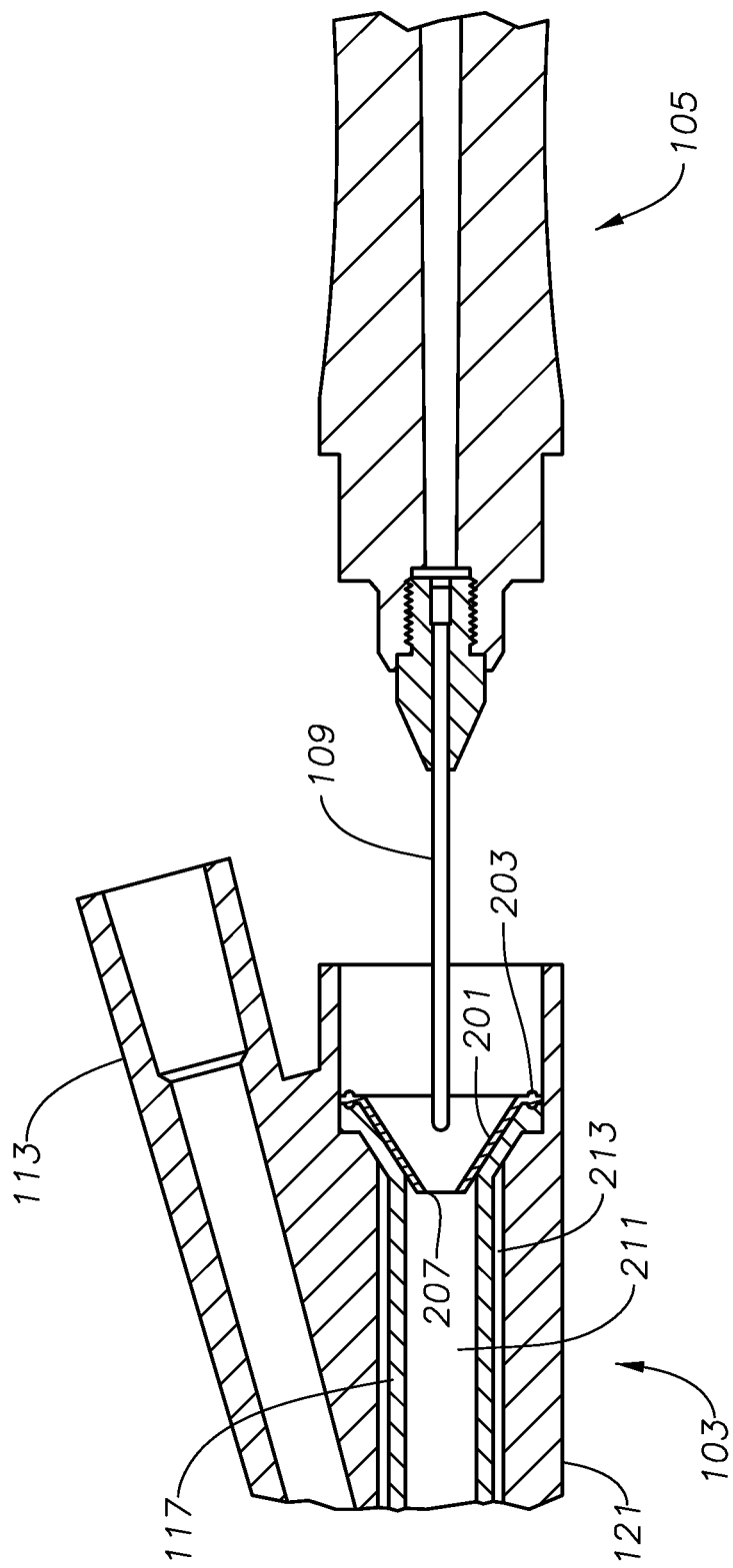
FIG. 2b illustrates a cross section of an alternate embodiment of the coupling portion of the irrigation handpiece portion.

FIG. 2b shows an alternate embodiment of irrigation handpiece portion 103 and aspiration handpiece portion 105. FIG. 2b shows a different profile for check valve 201 with a smaller base portion than shown in FIG. 2a. As shown in FIG. 2b, check valve 201 may include an axial O-ring 203 with a flat face on a side of the O-ring facing a corresponding flat face on aspiration tube 117. The rounded portion of O-ring 203 facing away from the flat face may be configured to axially press and seal against aspiration handpiece portion 105 when aspiration handpiece portion 105 is coupled to irrigation handpiece portion 103.

Figure 3A:
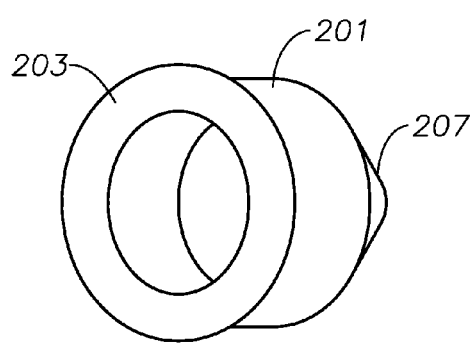
FIGS. 3a-g illustrate various embodiments of the check valve.
Figure 3B:
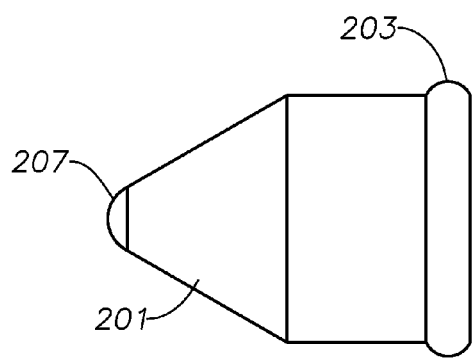
Figure 3C:
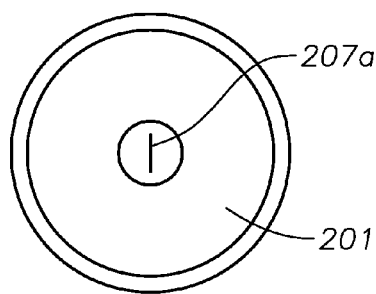
Figure 3D:
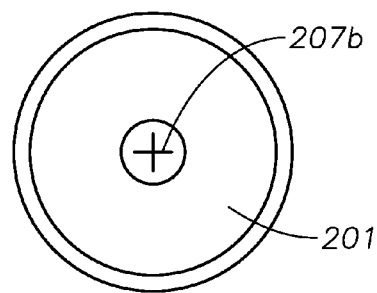
Figure 3E:
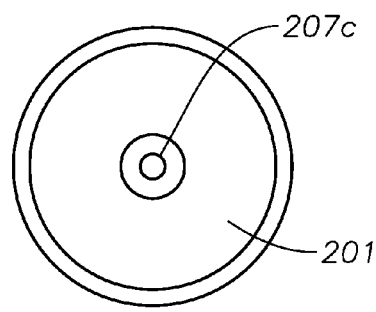
Figure 3G:
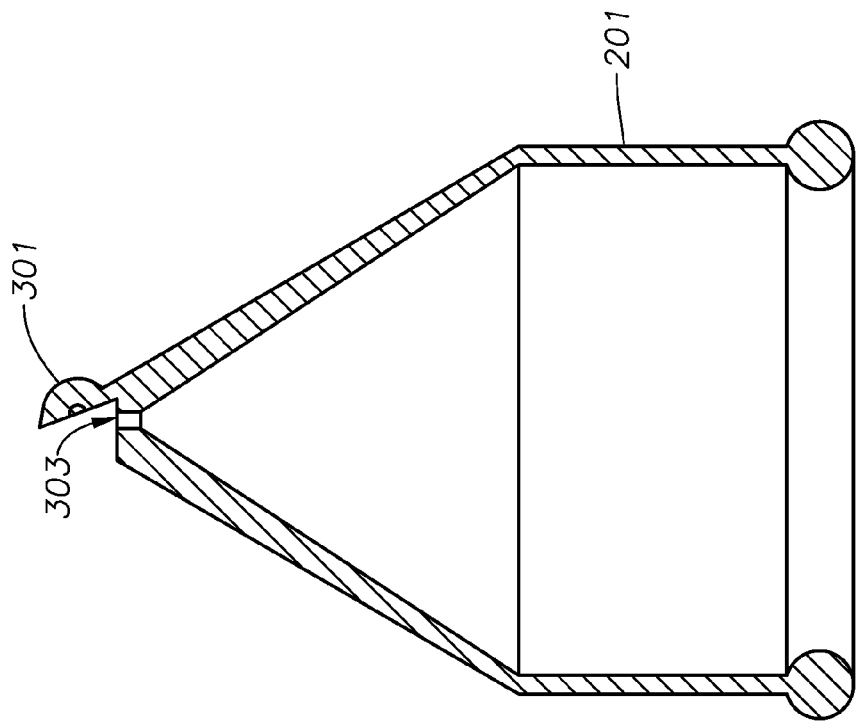
Figure 3F:
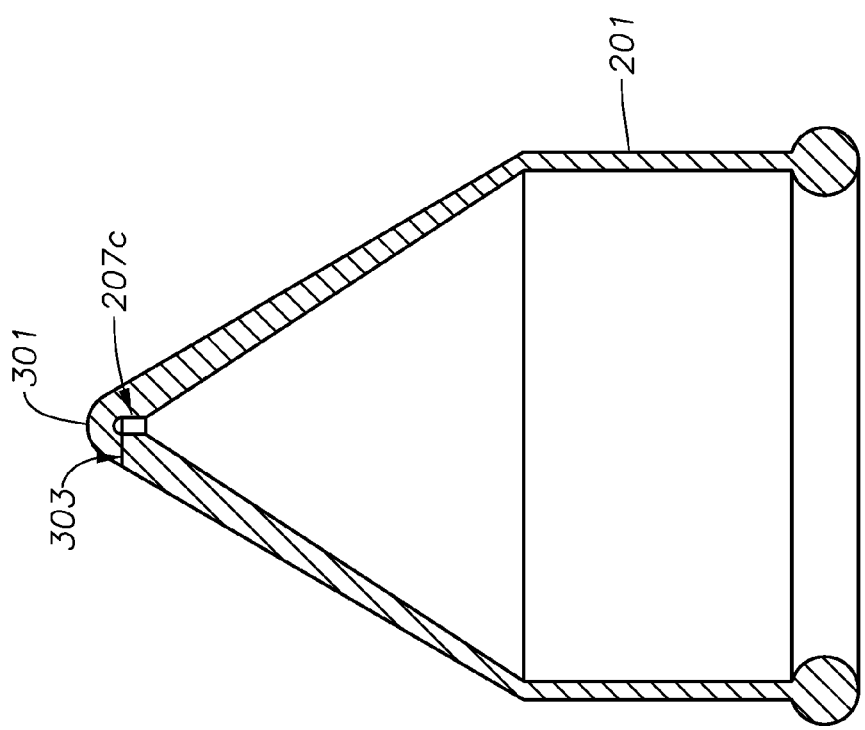

As seen in FIGS. 3a-b, in some embodiments, check valve 201 may be cone-shaped with aperture 207 in the tip of check valve 201 for aspiration tip 109 to pass through. In some embodiments, the aperture/tip interface may be snug such that aspiration fluid is inhibited from flowing around aspiration tip 109 when aspiration tip 109 is inserted into aperture 207. Further, aperture 207 may close or reduce in size when aspiration tip 109 is withdrawn to inhibit fluid flow through the reduced aperture when aspiration tip 109 is not present. For example, as shown in FIG. 3c, aperture 207 may be configured as a slit 207a in which both sides of slit 207a come together when aspiration tip 109 is withdrawn to prevent fluid passage through aperture 207. Aperture 207 may also include two crossing slits 207b as shown in FIG. 3d. Other aperture shapes are also contemplated (e.g., aperture 207 may be shaped as a small circular hole 207c as shown in FIG. 3e). As seen in FIGS. 3f-g, in some embodiments, check valve 201 may include a small circular aperture 207c with a hinged flap 301. Hinged flap 301 may be formed from a transverse slit 303 (transverse as seen in the cross section of FIGS. 3f-g). Hinged flap 301 may act as a flap valve to close to form a seal when aspiration tip 109 is not present. The pressure of any fluid present in aspiration tube chamber 211 will also act to press hinged flap 301 closed. Aperture 207c may have a depth (as shown) to allow a larger tolerance for the axial position of transverse slit 303.

In some embodiments, check valve 201 may include side walls that fit against the inner walls of aspiration tube 117 inside irrigation handpiece portion 103. The snug fit between the side walls of check valve 201 and the inner walls of aspiration tube 117 may inhibit aspiration fluid flow between check valve 201 and the inner walls of aspiration tube 117. O-ring 203 may provide an additional barrier to fluid flow by further inhibiting fluid flow between O-ring 203 and the inner walls of aspiration tube 117. In some embodiments, O-ring 203 and check valve 201 may be formed of a single piece (in some embodiments, O-ring 203 and check valve 201 may be separate pieces).

Figure 4B:
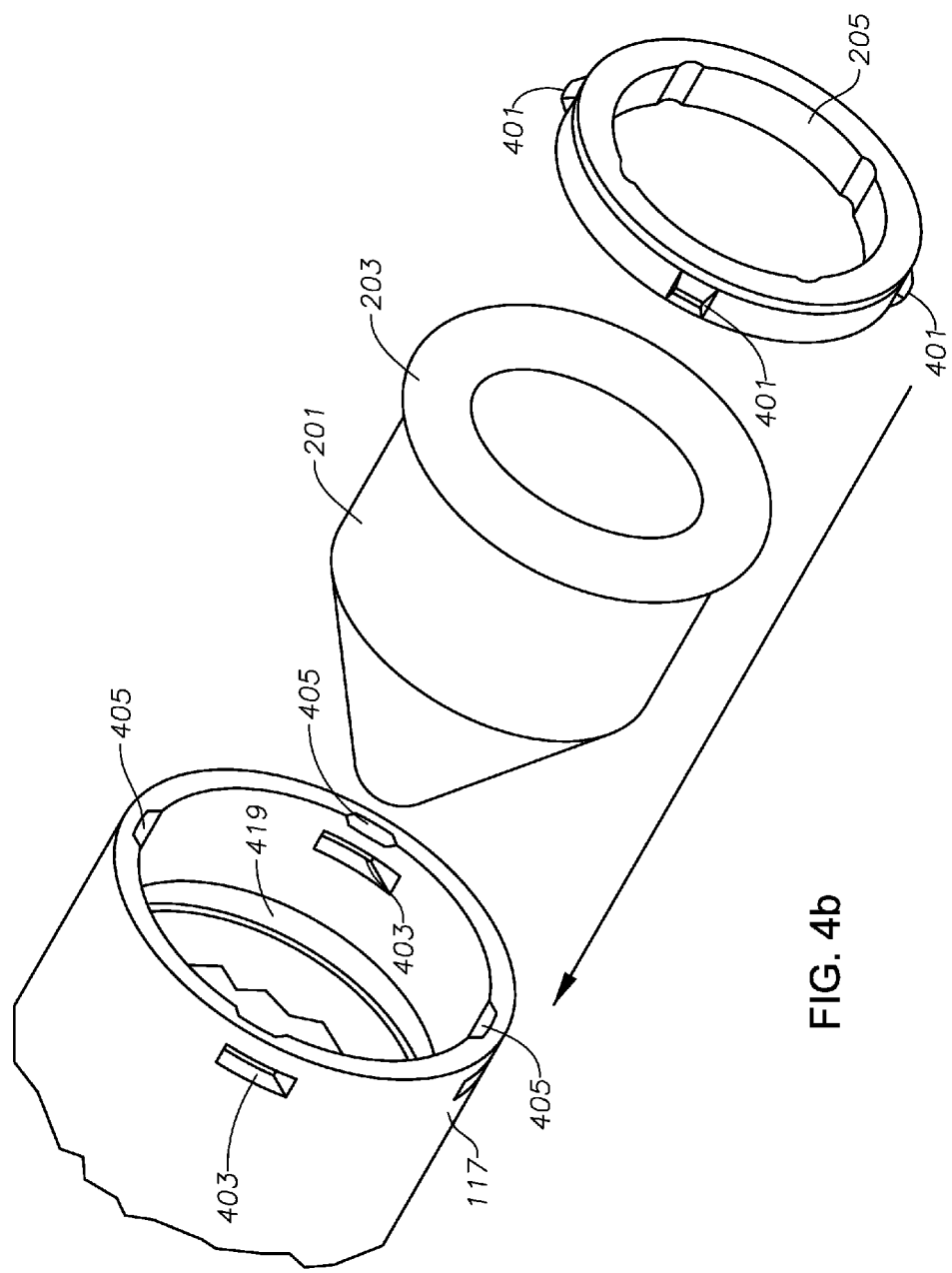
Figure 4C:
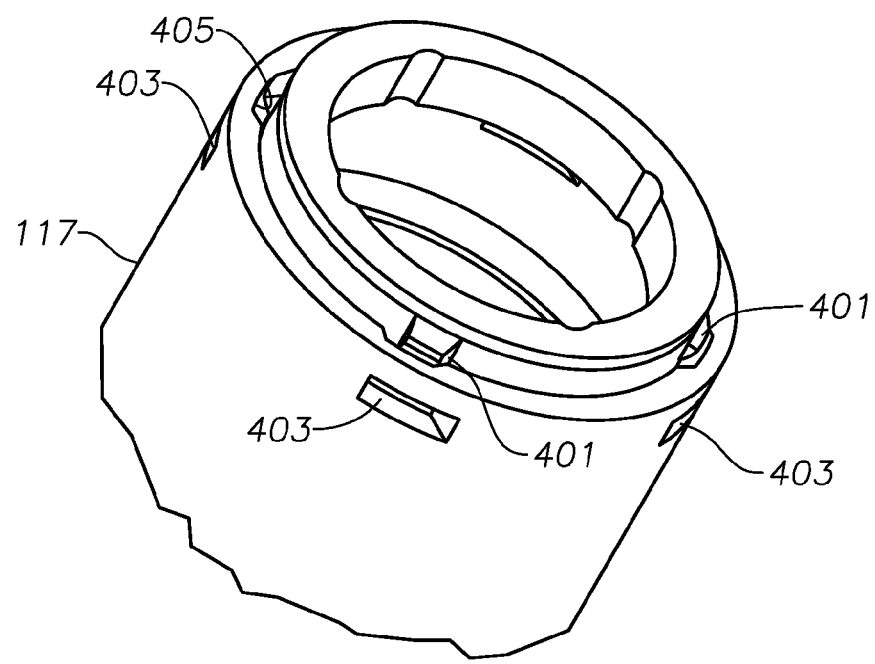
Figure 4D:
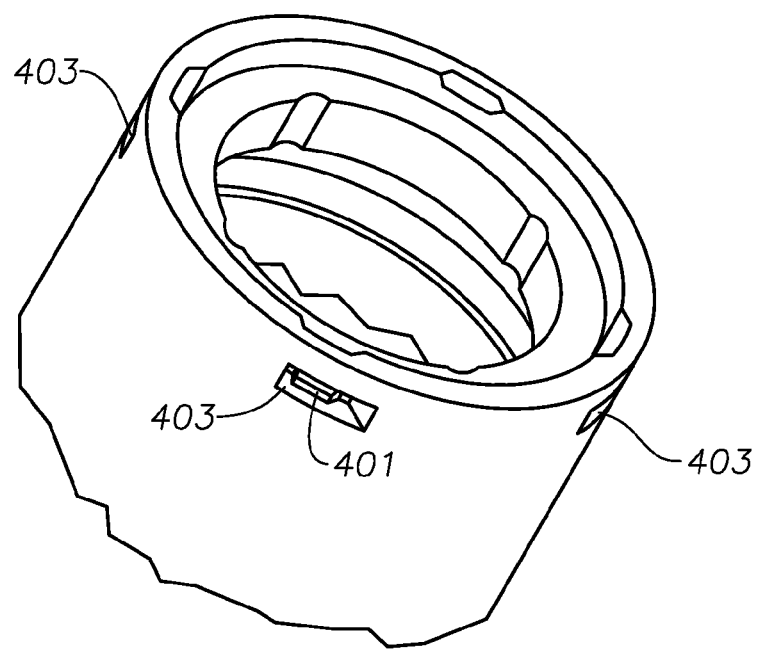

In some embodiments, snap-in retainer 205 may secure O-ring 203 and check valve 201 in irrigation handpiece portion 103 when aspiration handpiece portion 105 is separated from irrigation handpiece portion 103. As seen in FIGS. 4a-b, during assembly, check valve 201 and O-ring 203 may be inserted into aspiration tube 117 followed by snap-in retainer 205 which may have tabs 401 which snap into slots 403. As seen in FIG. 4c, in some embodiments, sub-slots 405 may be sized for tabs 401 to slide into prior to tabs 401 deforming slightly and then, as seen in FIG. 4d, snapping back into slots 403. As seen in FIG. 2a, once installed, snap-in retainer 205 may inhibit removal of check valve 201 and O-ring 203. In some embodiments, snap-in retainer 205 may abut O-ring 203 or may be slightly spaced from O-ring 203. As shown in the alternate embodiment of FIG. 2b, check valve 201 may not use snap-in retainer 205 (e.g., the friction fit between O-ring 203 and the side walls of outer irrigation handpiece casing 121 may retain check valve 201 inside outer irrigation handpiece casing 121 when aspiration handpiece portion 105 is removed).

Figure 5:
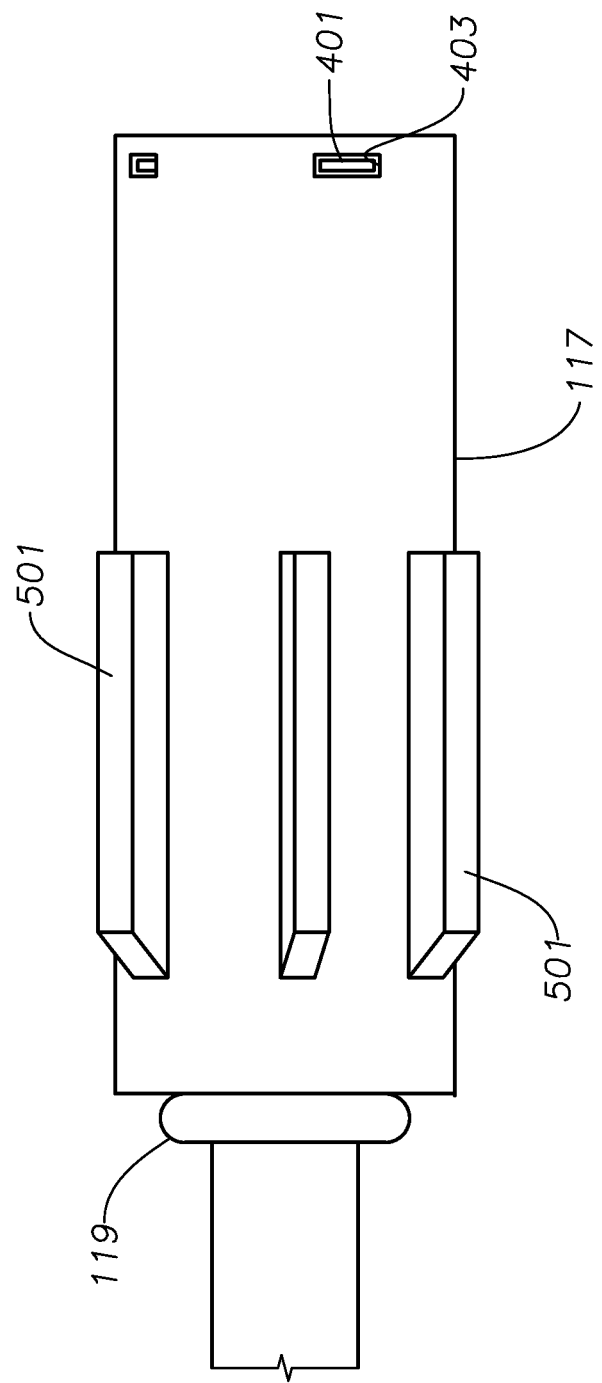
FIG. 5 illustrates the aspiration tube with an outer O-ring, according to an embodiment.
Figure 6A:
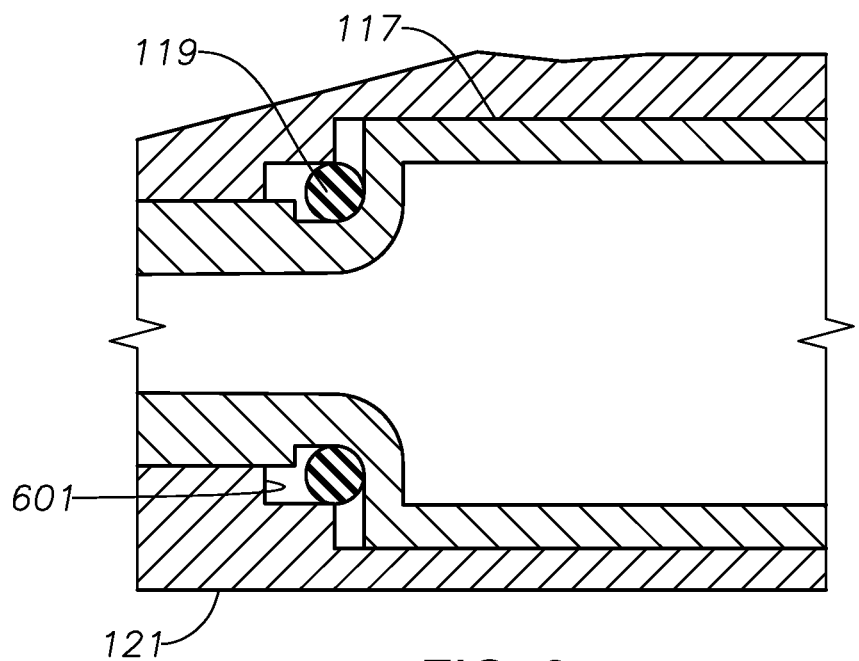
FIGS. 6a-b illustrate the snug fit between the outer O-ring on the aspiration tube and the inner wall of the outer irrigation handpiece casing, according to an embodiment.
Figure 6B:
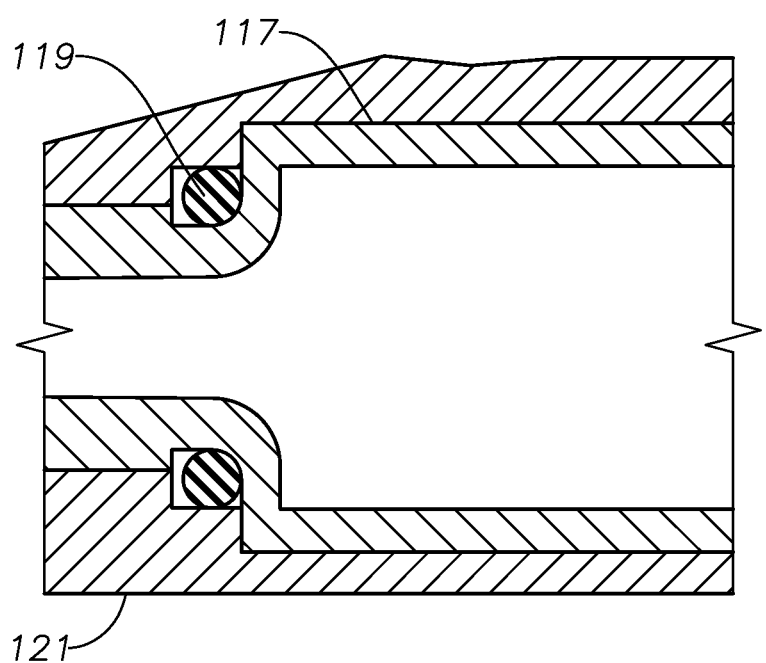

As seen in FIG. 5, aspiration tube 117 may include an additional O-ring 119. As seen in FIGS. 6a-b, O-ring 119 may provide a friction fit between aspiration tube 117 and outer irrigation handpiece casing 121. As O-ring 119/aspiration tube 117 assembly is inserted into outer irrigation handpiece casing 121, O-ring 119 may compress inside and form a fluid tight seal with a corresponding recess in outer irrigation handpiece casing 121. In some embodiments, the fluid tight seal may inhibit irrigation fluid entering irrigation handpiece portion 103 from connector 113 from exiting proximal end 131 of irrigation handpiece portion 103. The irrigation fluid may enter irrigation handpiece portion 103 from connector 113 and flow around the outside of aspiration tube 117 between O-ring 119 and sleeve 107. Ribs 407 (as seen in FIG. 4a) may space distal end 415 of aspiration tube 117 from the inner walls of the outer irrigation handpiece casing 121 to form a channel for the irrigation fluid. Irrigation fluid may then flow through opening 411 and around aspiration tip 111 that is screwed into distal end 415 of aspiration tube 117. Sleeve 107 may snap onto or screw onto ridge 409 of outer irrigation handpiece casing 121 and receive irrigation fluid from connector 113. Irrigation fluid may then leave sleeve 107 through an irrigation fluid outlet (e.g., port 129).

As seen in FIGS. 7a-d, aspiration handpiece portion 105 may form a separated handpiece portion dedicated to aspiration for a second incision. Fluid may enter aspiration tip 109 through an aspiration port 701 (both during bimanual and coaxial mode). Aspiration tip 109 on aspiration handpiece portion 105 is shown curved, but other shapes are also contemplated (e.g., straight, angled, etc.) In some embodiments, as seen in FIG. 2a, curved aspiration tip 109 may be curved or angled to reach various anatomical structures in the eye. In some embodiments, curved aspiration tip 109 may also be curved or angled toward a bottom wall of aspiration tube 117 to more easily reach aspiration fluid being pulled into aspiration tube chamber 211 (however, cannula device 101 will also function in coaxial mode with a straight aspiration tip 109). In some embodiments, aspiration tube chamber 211 may have a larger diameter than a forward portion of aspiration tube 117 to allow aspiration fluid to pool at second aspiration tip 109 (when the coaxial handpiece is being used at an angle) to be aspirated out of second aspiration tip 109 when cannula device 101 is in coaxial mode. A vacuum may be provided in aspiration tube 117 through aspiration tip 109 when cannula device 101 is in coaxial mode.

In some embodiments, aspiration tip 111 may include a sleeve 107 (such as a polymer sleeve) coupled to (e.g., overmolded onto, screwed onto, attached through adhesive, etc.) a needle (e.g., a stainless steel cannula). Other materials for sleeve 107 and needle are also contemplated. As seen in FIG. 1b, aspiration tip 111 may include a straight needle. As seen in FIG. 1c, aspiration tip 111 and sleeve 107 may be curved. In some embodiments, as seen in FIG. 1c, aspiration tip 111 and sleeve 107 may be curved in an opposite direction (i.e., a direction that points away) from a side of irrigation handpiece portion 103 with irrigation connector 113 as irrigation connector 113 will most likely extend on the top of a surgeon's grasp and the opposite curve of aspiration tip 111 and sleeve 107 will utilize the surgical "free" space below irrigation handpiece portion 103 ("free" in the sense that the space is not obstructed by the incoming irrigation line). As seen in FIG. 1d, aspiration tip 109 may also include a curved needle. Other needle shapes for aspiration tip 111 and aspiration tip 109 are also contemplated (e.g., angled, straight, etc.) Likewise, other sleeve shapes for sleeve 107 are also possible (e.g., angled, straight, etc.) In some embodiments, the needle for aspiration tip 111 may be bare or be overmolded by a polymer coating. In some embodiments, the needle for aspiration tip 109 may be bare or may be overmolded by a polymer coating.

As seen in FIG. 2a, in some embodiments, tubing connections to irrigation handpiece portion 103 may include various medical luer fittings. For example, tubing connection 113 may include a female locking luer as shown in FIG. 2a (e.g., to couple to male connector 209). Tubing connections to aspiration handpiece portion 105 may also include various medical luer fittings (e.g., male luer 115 on proximal end 137 of aspiration handpiece portion 105 to couple to female connector 127). Other connection types are also contemplated (e.g., as seen in FIG. 2b, connector 113 may be a female connector). Connector 113 may be configured to receive an irrigation line at an angle β (e.g., β may be approximately in a range of 10 degrees to 25 degrees) to reduce bends in the irrigation line (which may inhibit fluid flow) and make aspiration handpiece portion 105 or irrigation handpeice portion 103 easier to hold in the hand). Other β angles are also contemplated (e.g., β may be approximately in a range of between 5 degrees and 90 degrees). In some embodiments, aspiration luer 115 for aspiration may be on the end of aspiration handpiece portion 105 (other locations for luer 115 are also possible). Other tubing connections for the irrigation inlet and the aspiration outlet are also contemplated (e.g., friction fit, adhesive, etc.)

Figure 8:
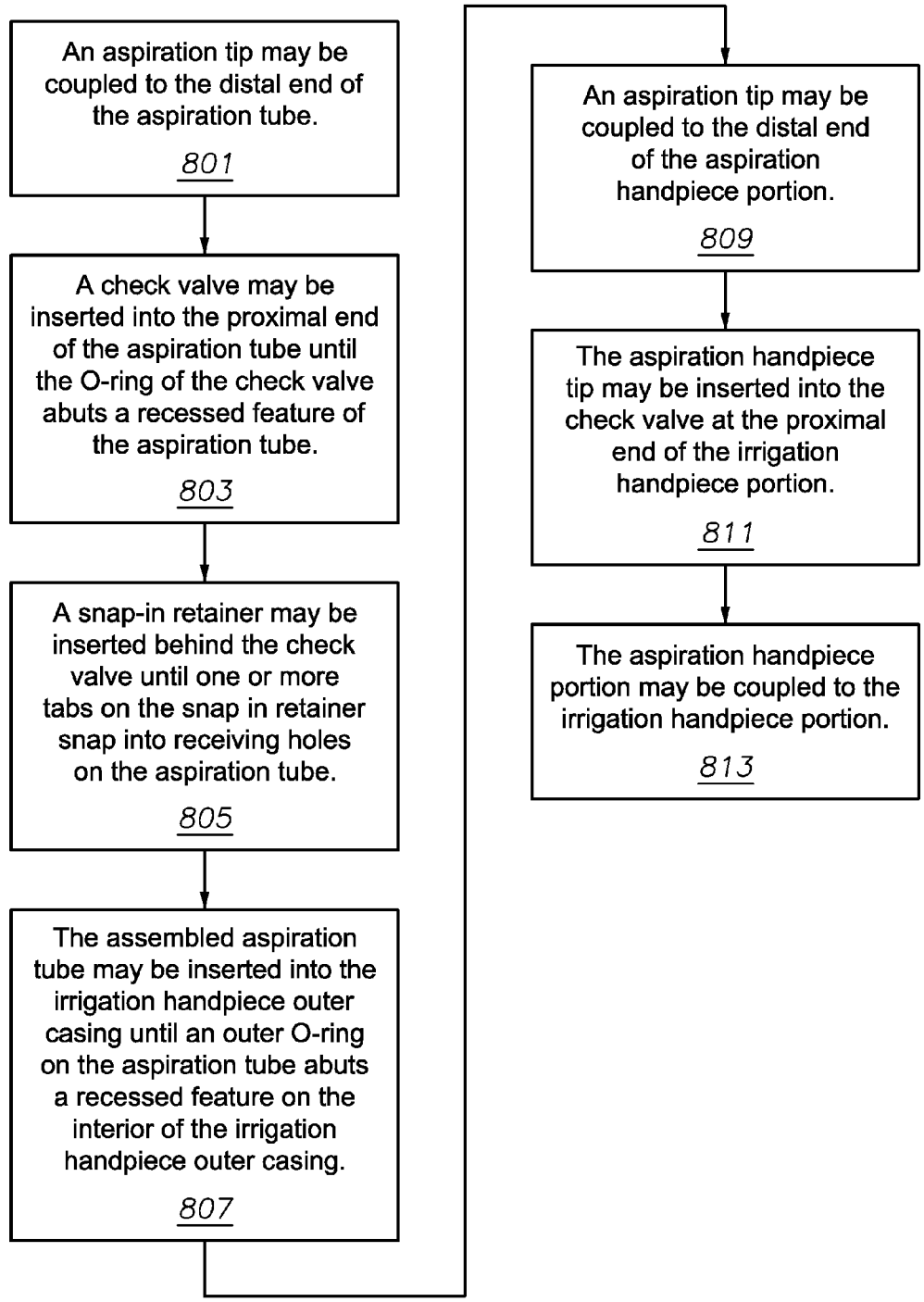
FIG. 8 illustrates a flowchart of a method for assembling the cannula device, according to an embodiment.

FIG. 8 illustrates a flowchart for a method of assembling cannula device 101. The elements provided in the flowchart are illustrative only. Various provided elements may be omitted, additional elements may be added, and/or various elements may be performed in a different order than provided below.

At 801, aspiration tip 111 may be coupled to distal end 415 of aspiration tube 117. For example, aspiration tip 111 may be screwed into an opening in aspiration tube 117.

At 803, check valve 201 may be inserted into proximal end 413 of aspiration tube 117 until O-ring 203 of check valve 201 abuts a recessed feature 419 of aspiration tube 117.

At 805, snap-in retainer 205 may be inserted behind check valve 201 until one or more tabs 401 on snap-in retainer 205 snap into receiving holes 403 on aspiration tube 117. Other attachment mechanisms for snap-in retainer 205 may be used. For example, snap-in retainer 205 may be coupled to aspiration tube 117 through an adhesive, a friction fit, etc. In some embodiments, snap-in retainer 205 may not be used (e.g., as seen in the embodiment shown in FIG. 2b).

At 807, assembled aspiration tube 117 may be inserted into irrigation handpiece outer casing 121 until outer O-ring 119 on aspiration tube 117 abuts recessed feature 601 on the interior of irrigation handpiece outer casing 121. In some embodiments, ribs 501 may be aligned with receiving grooves 213 on the interior of outer irrigation handpiece casing 121.

At 809, aspiration tip 109 may be coupled to distal end 135 of aspiration handpiece portion 105. For example, aspiration tip 109 may be screwed into receiving threads on aspiration handpiece portion 105.

At 811, aspiration handpiece tip 109 may be inserted into check valve 201 at proximal end 131 of irrigation handpiece portion 103. As seen in FIGS. 3c-3e, check valve 201 may include aperture 207 to allow aspiration handpiece tip 109 to pass through check valve 201.

At 813, aspiration handpiece portion 105 may be coupled to irrigation handpiece portion 103. For example, the end of aspiration handpiece portion 105 may be inserted into proximal end 131 of irrigation handpiece portion 103 and then twisted to engage tab 123 on the aspiration handpiece portion 105 with slot 125 on irrigation handpiece portion 103. In some embodiments, irrigation handpiece portion 103 may have tab 123 and aspiration handpiece portion 105 may have slot 125. Other coupling techniques are also possible (e.g., a friction fit between irrigation handpiece portion 103 and aspiration handpiece portion 105).

The elements of flowchart 801-813 may also be reversed to disassemble the cannula device 101. Assembly/disassembly may allow parts or all of the cannula device 101 to be cleaned and/or sterilized in order to be reusable. In some embodiments, parts of the cannula device 101 may be reused while other parts (e.g., the aspiration tips 109 and/or 111) may be disposed of between uses (with new tips installed for each subsequent use). In some embodiments, the entire cannula device 101 may be disposable. In some embodiments, the entire cannula device 101 may be reusable.

Figure 9:
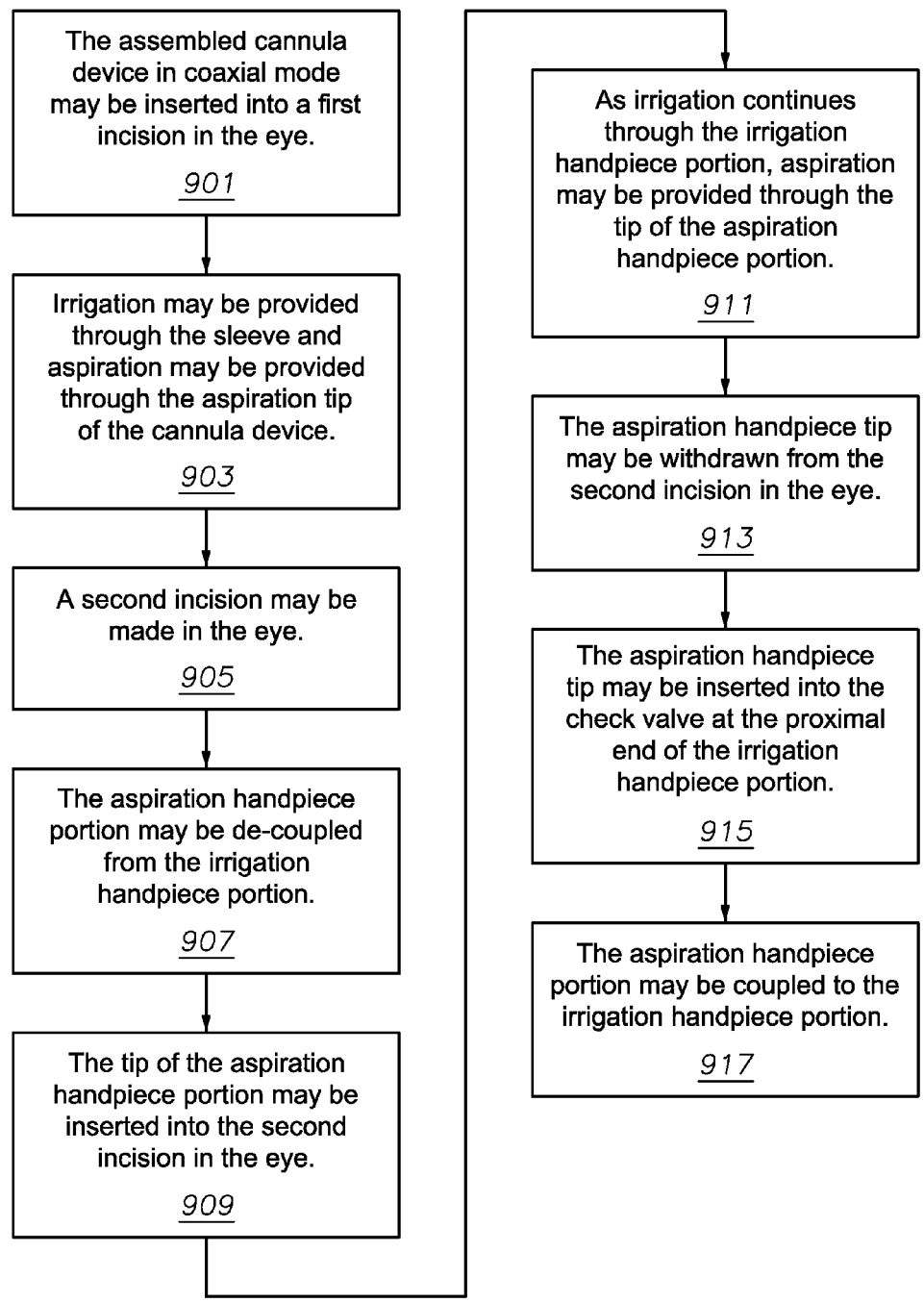
FIG. 9 illustrates a flowchart of a method for transforming the cannula device between coaxial and bimanual modes, according to an embodiment.

FIG. 9 illustrates a flowchart for a method of using cannula device 101. The elements provided in the flowchart are illustrative only. Various provided elements may be omitted, additional elements may be added, and/or various elements may be performed in a different order than provided below.

Figure 10:
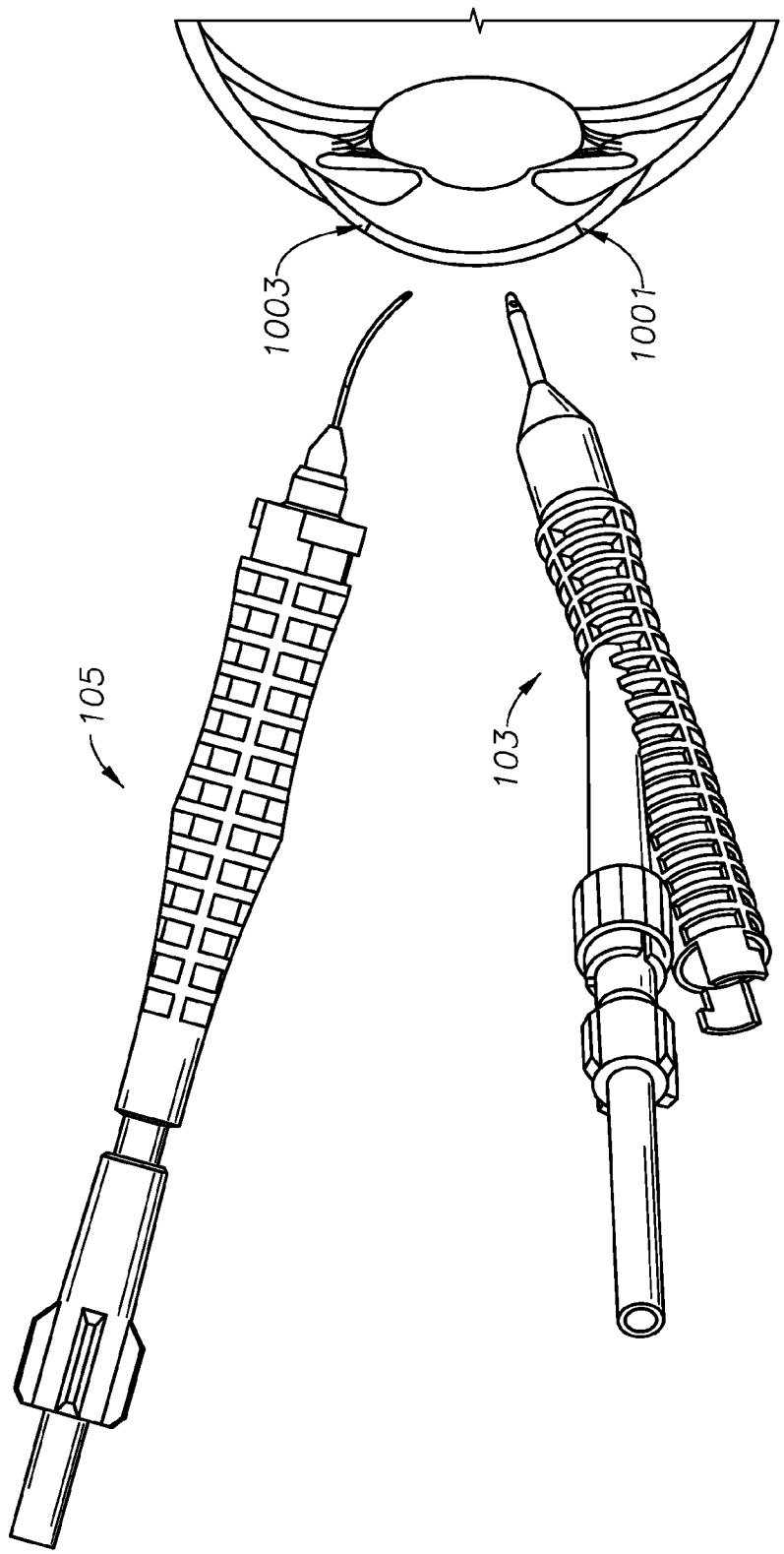
FIG. 10 illustrates the cannula device in bimanual mode, according to an embodiment.

At 901, assembled cannula device 101 in coaxial mode may be inserted into first incision 1001 in the eye (e.g. see incision 1001 in FIG. 10).

At 903, irrigation may be provided through sleeve 107 and aspiration may be provided through aspiration tip 111 of cannula device 101.

At 905, second incision 1003 may be made in the eye.

At 907, aspiration handpiece portion 105 may be decoupled from irrigation handpiece portion 103. For example, as seen in FIG. 1d, aspiration handpiece portion 105 may be twisted to disengage tab 123 on aspiration handpiece portion 105 from slot 125 in irrigation handpiece portion 103 and then axially pulled to separate aspiration handpiece portion 105 from irrigation handpiece portion 103. In some embodiments, aspiration handpiece portion 105 may be removed from irrigation handpiece portion 103 while sleeve 107 and tip 111 remain in incision 1001. In some embodiments, sleeve 107 and tip 111 may be withdrawn from incision 1001 prior to removing aspiration handpiece portion 105 from irrigation handpiece portion 103.

At 909, tip 109 of aspiration handpiece portion 105 may be inserted into second incision 1003 in the eye.

At 911, as irrigation continues through irrigation handpiece portion 103 through sleeve 107, aspiration may be provided through tip 109 of aspiration handpiece portion 105 in second incision 1003.

At 913, aspiration handpiece tip 109 may be withdrawn from second incision 1003 in the eye.

At 915, aspiration handpiece tip 109 may be inserted into check valve 201 at proximal end 131 of irrigation handpiece portion 103.

At 917, aspiration handpiece portion 105 may be coupled to irrigation handpiece portion 103. In some embodiments, aspiration handpiece portion 105 may be coupled to irrigation handpiece portion 103 while sleeve 107 and tip 111 remain in incision 1001. In some embodiments, sleeve 107 and tip 111 may be withdrawn from incision 1001 prior to coupling aspiration handpiece portion 105 to irrigation handpiece portion 103.

Various modifications may be made to the presented embodiments by a person of ordinary skill in the art. Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A cannula device, comprising:
   an irrigation handpiece portion comprising a first aspiration tip configured to provide aspiration and an irrigation fluid outlet configured to provide an irrigation fluid;
   an aspiration handpiece portion comprising a second aspiration tip configured to provide aspiration, wherein the second aspiration tip extends from a distal end of the aspiration handpiece portion;
   wherein the cannula device is transformable between:
   a coaxial mode in which the aspiration handpiece portion is coupled to the irrigation handpiece portion such that fluid is aspirated through the first aspiration tip and then the second aspiration tip in series and the irrigation fluid is provided through the irrigation fluid outlet, and
   a bimanual mode in which the aspiration handpiece portion is separated from the irrigation handpiece portion to provide aspiration through the second aspiration tip while the irrigation handpiece portion continues to provide the irrigation fluid through the irrigation fluid outlet but not aspiration through the first aspiration tip.

2. The cannula device of claim 1, wherein the irrigation fluid outlet is a port in an irrigation sleeve coupled to a distal end of the irrigation handpiece portion, wherein the irrigation sleeve at least partially surrounds the first aspiration tip extending from the irrigation handpiece portion.

3. The cannula device of claim 1, further comprising a seal in a proximal end of the irrigation handpiece portion, wherein the seal is configured to receive the second aspiration tip when the aspiration handpiece portion is coupled to the irrigation handpiece portion.

4. The cannula device of claim 3, wherein the seal is cone-shaped and configured to fit within the proximal end of the irrigation handpiece portion such that walls of the seal press against an inner wall of the irrigation handpiece portion to inhibit fluid flow between the walls of the seal and the inner wall of the irrigation handpiece portion.

5. The cannula device of claim 3, wherein the seal comprises an O-ring configured to press against an inner wall of the irrigation handpiece portion to inhibit fluid flow between the O-ring and the inner wall of the irrigation handpiece portion.

6. The cannula device of claim 3, wherein the seal is configured to inhibit aspiration fluid flow out of the irrigation handpiece portion when the aspiration handpiece portion is removed from the irrigation handpiece portion.

7. The cannula device of claim 3, further comprising a retainer to retain the seal in the irrigation handpiece portion as the aspiration handpiece portion is inserted and withdrawn from the irrigation handpiece portion.

8. The cannula device of claim 1, wherein the irrigation handpiece portion and the aspiration handpiece portion include interlocking elements for releasably coupling the distal end of the aspiration handpiece portion to a proximal end of the irrigation handpiece portion.

9. The cannula device of claim 1, wherein the irrigation handpiece portion further comprises an irrigation connector configured to couple to an irrigation line providing the irrigation fluid to the irrigation handpiece portion and wherein the second aspiration tip is curved in a direction that points away from a side of the irrigation handpiece portion comprising the irrigation connector.

10. A method, comprising:
    inserting an aspiration tip of an aspiration handpiece portion into a seal in an irrigation handpiece portion to place the aspiration tip of the aspiration handpiece portion in fluid communication with an aspiration pathway of the irrigation handpiece portion such that fluid entering an aspiration tip on the irrigation handpiece portion passes through an interior of the irrigation handpiece portion, into the aspiration tip of the aspiration handpiece portion, and then out of the aspiration handpiece portion;
    coupling the aspiration handpiece portion to the irrigation handpiece portion to form a coaxial handpiece;
    providing aspiration through the aspiration tip on the irrigation handpiece portion and irrigation fluid through an irrigation fluid outlet on the irrigation handpiece portion;
    decoupling the aspiration handpiece portion from the irrigation handpiece portion;
    withdrawing the aspiration tip of the aspiration handpiece portion from the seal in the irrigation handpiece portion to form two separate handpieces; and
    providing the irrigation fluid through the irrigation fluid outlet on the irrigation handpiece portion and aspiration through the aspiration tip on the aspiration handpiece portion.

11. The method of claim 10, wherein providing the irrigation fluid through the irrigation fluid outlet comprises providing the irrigation fluid through a port in an irrigation sleeve coupled to a distal end of the irrigation handpiece portion, wherein the irrigation sleeve at least partially surrounds the aspiration tip on the irrigation handpiece portion.

12. The method of claim 10, wherein coupling the aspiration handpiece portion to the irrigation handpiece portion comprises twisting together interlocking elements on the aspiration handpiece portion and the irrigation handpiece portion.

13. The method of claim 10, wherein coupling the aspiration handpiece portion to the irrigation handpiece portion and decoupling the aspiration handpiece portion from the irrigation handpiece portion does not require removing irrigation or aspiration tubing connections and does not require removing a sleeve from the irrigation handpiece portion.

14. The cannula device of claim 1, wherein both the first and second aspiration tip are curved.

15. The cannula device of claim 1,
    wherein the irrigation handpiece portion further comprises a sleeve having a distal end and a proximal end, wherein the proximal end is coupled to the irrigation handpiece portion and wherein the irrigation fluid exits the sleeve through the distal end, and
    wherein in the coaxial mode, the first aspiration tip extends to the distal end of the infusion sleeve.

* * * * *

UNITED STATES PATENT AND TRADEMARK OFFICE
CERTIFICATE OF CORRECTION

PATENT NO. : 9,839,738 B2
APPLICATION NO. : 14/272784
DATED : December 12, 2017
INVENTOR(S) : Beauvais et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 139 days.

Signed and Sealed this
Twenty-fifth Day of September, 2018

Andrei Iancu
*Director of the United States Patent and Trademark Office*